United States Patent
Rohloff et al.

(10) Patent No.: US 9,163,056 B2
(45) Date of Patent: Oct. 20, 2015

(54) 5-POSITION MODIFIED PYRIMIDINES AND THEIR USE

(71) Applicant: SomaLogic, Inc., Boulder, CO (US)

(72) Inventors: John Rohloff, Boulder, CO (US); Nebojsa Janjic, Boulder, CO (US); Jeffrey D. Carter, Longmont, CO (US); Catherine Fowler, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 14/069,798

(22) Filed: Nov. 1, 2013

(65) Prior Publication Data

US 2014/0058076 A1     Feb. 27, 2014

Related U.S. Application Data

(63) Continuation of application No. 13/085,256, filed on Apr. 12, 2011, now abandoned.

(60) Provisional application No. 61/323,145, filed on Apr. 12, 2010.

(51) Int. Cl.
| | |
|---|---|
| C07H 19/06 | (2006.01) |
| C07H 19/067 | (2006.01) |
| C07H 19/073 | (2006.01) |
| C07H 19/10 | (2006.01) |
| C07H 21/04 | (2006.01) |
| C12N 15/115 | (2010.01) |

(52) U.S. Cl.
CPC ............... *C07H 19/06* (2013.01); *C07H 19/10* (2013.01); *C07H 21/04* (2013.01); *C12N 15/115* (2013.01); *C12N 2310/335* (2013.01)

(58) Field of Classification Search
CPC .... C07H 19/06; C07H 19/067; C07H 19/073; C07H 19/10; C07H 19/67
USPC .................... 536/26.14, 26.2, 26.21
See application file for complete search history.

(56) References Cited

U.S. PATENT DOCUMENTS

| | | |
|---|---|---|
| 4,267,171 A | 5/1981 | Bergstrom et al. |
| 4,415,732 A | 11/1983 | Caruthers et al. |
| 4,594,339 A | 6/1986 | Lopez et al. |
| 4,711,955 A | 12/1987 | Ward |
| 4,725,677 A | 2/1988 | Koster |
| 4,828,979 A | 5/1989 | Kelvan et al. |
| 4,948,882 A | 8/1990 | Ruth |
| 4,997,818 A | 3/1991 | McCaffrey et al. |
| 5,023,243 A | 6/1991 | Tullis |
| 5,047,519 A | 9/1991 | Hobbs, Jr. et al. |
| 5,093,232 A | 3/1992 | Urdea et al. |
| 5,118,672 A | 6/1992 | Schinazi et al. |
| 5,134,066 A | 7/1992 | Rogers et al. |
| 5,138,045 A | 8/1992 | Cook et al. |
| 5,428,149 A | 6/1995 | Eaton |
| 5,576,429 A | 11/1996 | Johansson et al. |
| 5,580,972 A | 12/1996 | Tu |
| 5,582,981 A | 12/1996 | Toole et al. |
| 5,591,843 A | 1/1997 | Eaton et al. |
| 5,595,877 A | 1/1997 | Gold et al. |
| 5,596,091 A | 1/1997 | Switzer |
| 5,633,361 A | 5/1997 | Eaton et al. |
| 5,645,985 A | 7/1997 | Froehler |
| 5,658,738 A | 8/1997 | Nadeau et al. |
| 5,660,985 A | 8/1997 | Pieken et al. |
| 5,719,273 A | 2/1998 | Tu et al. |
| 5,801,154 A | 9/1998 | Baracchini et al. |
| 5,817,785 A | 10/1998 | Gold et al. |
| 5,840,867 A | 11/1998 | Toole et al. |
| 5,945,527 A * | 8/1999 | Tu et al. ................ 536/27.6 |
| 5,958,691 A | 9/1999 | Pieken |
| 6,020,483 A | 2/2000 | Beckvermit et al. |
| 6,030,776 A | 2/2000 | Eaton et al. |
| 6,175,001 B1 | 1/2001 | Barbas et al. |
| 6,184,364 B1 | 2/2001 | Pieken |
| 6,344,318 B1 | 2/2002 | Gold et al. |
| 6,355,787 B1 | 3/2002 | Beckvermit et al. |
| 6,716,583 B2 | 4/2004 | Gold et al. |
| 7,094,770 B2 | 8/2006 | Watanabe et al. |
| 7,855,054 B2 | 12/2010 | Schneider et al. |
| 7,947,447 B2 | 5/2011 | Zichi et al. |
| 8,404,830 B2 | 3/2013 | Zichi et al. |
| 2003/0144231 A1 | 7/2003 | Wengel et al. |
| 2005/0130195 A1 | 6/2005 | Fujihara et al. |
| 2005/0227225 A1 | 10/2005 | Krevolin |
| 2005/0288244 A1 | 12/2005 | Manoharan et al. |
| 2006/0057573 A1 | 3/2006 | Gold et al. |

(Continued)

FOREIGN PATENT DOCUMENTS

| | | |
|---|---|---|
| JP | Hei 5-500799 A | 2/1993 |
| JP | 2000-327694 A | 11/2000 |

(Continued)

OTHER PUBLICATIONS

Holmes et al. European Journal of Chemistry, 24, 5171-5183, 2005.*
IPRP issued Oct. 26, 2012 in PCT/US2011/032143.
Nomura et al. (1997) Nucleic Acids Research 25(14):2784-2791, "Site-specific introduction of functional groups into phosphodiester oligodeoxynucleotides and their thermal stability and nuclease-resistance properties".
Ito et al. (2003) Nucleic Acids Research 31(10):2514-2523, "Synthesis, thermal stability and resistance to enzymatic hydrolysis of the oligonucleotides containing 5-(*N*-aminohexyl)carbamoyl-2'-*O*-methylurindines".
Ueno et al. (1997) Nucleic Acids Research 25(19):3777-3782, "Effects of 5-(*N*-aminohexyl)carbamoyl-2'-deoxyuridine on endonuclease stability and the ability of oligodeoxynucleotide to activate RNase H".

(Continued)

*Primary Examiner* — Venkataraman Balasubramanian
(74) *Attorney, Agent, or Firm* — Swanson & Bratschun, L.L.C.

(57) ABSTRACT

The present disclosure relates to the field of nucleic acid chemistry, specifically to 5-position modified uridines as well as phosphoramidite and triphosphate derivatives thereof. The present disclosure also relates to methods of making and using the same.

3 Claims, No Drawings

(56) References Cited

U.S. PATENT DOCUMENTS

| | | |
|---|---|---|
| 2007/0041901 A1 | 2/2007 | Diener et al. |
| 2007/0166741 A1 | 7/2007 | Heil et al. |
| 2008/0194502 A1 | 8/2008 | Dellinger et al. |
| 2009/0004667 A1* | 1/2009 | Zichi et al. ............... 435/6 |
| 2009/0098549 A1 | 4/2009 | Schneider et al. |
| 2010/0285479 A1 | 11/2010 | Jenison |
| 2011/0082286 A1 | 4/2011 | Zichi et al. |
| 2011/0136099 A1 | 6/2011 | Schneider et al. |
| 2011/0275794 A1 | 11/2011 | Rohloff et al. |
| 2014/0249043 A1 | 9/2014 | Schneider et al. |

FOREIGN PATENT DOCUMENTS

| | | |
|---|---|---|
| JP | 2004-238353 A | 8/2004 |
| WO | WO 90/15065 | 12/1990 |
| WO | WO 91/13900 | 9/1991 |
| WO | WO 2006/063717 | 6/2006 |
| WO | WO 2008/078180 A2 | 7/2008 |
| WO | WO 2008/104408 | 9/2008 |
| WO | WO 2008/137776 A2 | 11/2008 |
| WO | WO 2011/109642 | 9/2011 |
| WO | WO 2012/061810 | 5/2012 |
| WO | WO 2015/077292 | 5/2015 |

OTHER PUBLICATIONS

Gold et al. (Dec. 7, 2010) PLOS ONE 5(12):1-17, (e15004), "Aptamer-Based Multiplexed Proteomic Technology for Biomarker Discovery".

European Search Report issued Sep. 25, 2013 in EP 11769451.3.

Agathocleous and Shaw (1991) J. Chem. Soc. Perkin Trans. 1: 2317-2321, "Purines, pyrimidines and imidazoles. Part 66. New Synthesis of some uridine and N-alkoxycarbonyl 5-carboxyamides, N-carbomoyl 5-carboxyamides and 5-carboxyamides".

Agris et al. (1995) Biochimie 771(1-2):125-134, "Site-selected introduciton of modified purine and pyrimidine ribonucleosides into RNA by automated phosphoramidite chemistry".

Bergstrom and Ruth (1976) J. Amer. Chem. Soc. 98(6): 1587-1589, "Synthesis of C-5 substituted pyrimidine nucleosides via organopalladium intermediates".

Bergstrom et al. (1982) J. Org. Chem. 47(11): 2174-2178,"Pyrido[2,3-d]pyrimidine nucleosides. Synthesis via cyclization of C-5-substituted cytidines".

Bier and Fürste, (Feb. 1997) EXS 80:97-120, "Nucleic Acid based sensors".

Bigge and Mertes (1981) J. Org. Chem. 46(10): 1994-1997, "A palladium-catalyzed coupling reaction and a photolytic reaction for the direct synthesis of 5-arylpyrimidine nucleotides".

Brodsky (2002) Mol. Cell. Proteomics 1(12):922-929, "A Microbead-based System for Identifying and Characterizing RNA-Protein Interactions by Flow Cytometry".

Crisp (1989) Synthetic Communications 19: 2117-2123, "Synthesis of 5-alkenyl-2' deoxyuridines via organostannanes".

Crisp and Flynn (1990) Tetrahedron Letters 31(9):1347-1350, "Palladium-catalysed coupling of uridine triflate with organostannanes".

Crouch and Eaton (1994) Nucleosides & Nucleotides 13(4): 939-944, "Synthesis of 2'deoxyuridine nucleosides with appended 5-position carbonyl cross-linking groups".

Dewey et al. (1995) J. Am. Chem. Soc. 117: 8474-8475, "New Uridine Derivatives for Systematic Evolution of RNA Ligands by Exponential Enrichment".

DiDonato (2006) "Dissertation. Part II. Synthesis and Evaluation of Modified Nucleotides for DNA Aptamer Selection" University of North Carolina, Raleigh 30-53.

Eaton et al. (1997) Bioorganic & Medicinal Chemistry 5(6):1087-1096, "Post-SELEX Combinatorial Optimization of Aptamers".

EP Search report issued Dec. 1, 2009 in EP application serial No. 08782010.6.

EP Search report issued Feb. 22, 2010 in EP application serial No. 09012809.1.

Goodchild et al. (1983) J. Med. Chem. 26(9): 1252-1257, "Structural Requirements of Olefinic 5-Substituted Deoxyuridines for Antiherpes Activity".

Hobbs et al. (1973) Biochemistry 12(25): 5138-5145, "Polynucleotides Containing 2'-Amino-2'deoxyribose and 2'-Azido-2'deoxyribose".

Holy (1972) Collection Czechoslov. Chem. Commun. 37: 1555-1576, "Nucleic acid components and their analogues. CXLVII. Preparation of 5-ethoxycarbonyluridine, 5-carboxyuridine and their nucleotide derivatives".

Ikehara and Tada (1968) Synthetic Procedures in Nucleic Acid Chemistry (Zorbach and Tipson, eds) 1: 189-193, "2'-Deoxyadenosine and 3'-Deoxyadenosine (Cordycepin)".

IPRP issued Jan. 19, 2010 in PCT/US2008/070383.

ISR and Written Opinion issued Aug. 26, 2011 in PCT/US2011/032143.

ISR and Written Opinion mailed Dec. 17, 2008 in PCT/US2008/070383.

Kerr et al. (Feb. 9, 2000) Journal of Physical Chemistry B, 104(9):2166-2175, "Synthesis and Photophysics of a 1-Pyrenylmethyi-Substituted 2'-Deoxyuridine-5-Carboxamide Nucleoside:Electron-Transfer Product Lifetimes and Energies".

Kerr et al., (Feb. 9, 2000) Journal of Physical Chemistry B, 104(9):2166-2175, "Synthesis and Photophysics of a 1-Pyrenylmethyi-Substituted 2'-Deoxyuridine-5-Carboxamide Nucleoside: Electron-Transfer Product Lifetimes and Energies".

Latham et al. (1994)Nucleic Acids Research 22(14):2817-2822, "The application of a modified nucleotide in aptamer selection: novel thrombin aptamers containing 5-(1-pentynyl)-2'-deoxyuridine".

Mamos et al. (1992) Tetrahedron Letters 33(17): 2413-2416, "Straightforward C-8 alkylation of adenosine analogues with tetraalkyltin reagents".

Matsuda et al. (1979) Chemical and Pharmaceutical Bulletin, Pharmaceutical Society of Japan, Tokyo, JP 27(1): 183-192, "Nucleosides and nucleotides. XXVII. Synthesis of 2- and 8-cyanoadenosines and their derivatives".

Molecular Probes Handbook, 8th Edition, Section 8.2 (2001) "Labeling Oligonucleotides and Nucleic Acids".

Office Action issued Jun. 9, 2010 in U.S. Appl. No. 12/175,446.

Ono et al. (1994) Bioorg. & Med. Chem. Let. 4(2): 361-366, "Nucleosides and Nucleotides. 127. A novel and convenient post-synthetic modification method for the synthesis of oligodeoxyribonucleotides carrying amino linkers at the 5-position of 2'deoxyuridine".

Perlman et al. (1985) J. Med. Chem. 28(6): 741-748, "Nucleosides. 133. Synthesis of 5-alkenyl-1-(2-deoxy-2-fluoro-β-D-arabinofuranosyl) cytosines and related pyrimidine nucleosides as potential antiviral agents".

Ruth and Bergstrom (1978) J. Org. Chem. 43(14): 2870-2876, "C-5 substituted pyrimidine nucleosides. 1. Synthesis of C-5 allyl, propyl, and propenyl uracil and cytosine nucleosides via organopalladium intermediates".

Sagi et al. (1994) J. Med. Chem. 37: 1307-1311, "Synthesis and antiviral activities of 8-alkynyl-, 8-alkenyl-, and 8-alkyl-2'-deoxyadenosine analogues".

Saitoh et al. (2002) Nucleic Acids Research Supplement 2:215-216 "Modified DNA aptamers against sweet agent aspartame".

Seelig and Jaschke (1997) Tetrahedron Letters, 38(44):7729-7732, "Site-Specific Modification of Enzymatically Synthesized RNA: Transcription Initiation and Diels-Alder Reaction".

Silverman, R. B., "Bioisosterism," part of Chapter II of The Organic Chemistry of Drug Design and Drug Action, Academic Press, 1992, New York, NY, only pp. 4 and 19-23 supplied.

Tronchet et al. (1988) Nucleosides and Nucleotides, 7(2): 249-269, "3'-deoxy-3'-hydroxyamino-β-D-xylofuranosyluracil and derivatives thereof".

(56) References Cited

OTHER PUBLICATIONS

Uhlmann and Peyman (Jun. 1990) Chemical Reviews 90(4):544-584, "Antisense Oligonucleotides: A New Therapeutic Principle".

Van Aerschot et al. (1993) J. Med. Chem. 36: 2938-2942, "Antiviral activity of C-alkylated purine nucleosides obtained by cross-coupling with tetraalkyltin reagents".

Vaught et al. (Mar. 2010) J.Am. Chem. Soc. ePub, 132(12):4141-4151:4142, "Expanding the Chemistry of DNA for In Vitro Selection".

Vaught, Jonathan David, Thesis Oct. 2008, "Enhancing the Functionality of Nucleic Acids".

El Safadi et al. (2010) J. Med. Chem. 53:1534-1545, "5-Modified-2'-dU and 2'-dC as Mutagenic Anti HIV-1 Proliferation Agents: Synthesis and Activity".

* cited by examiner

5-POSITION MODIFIED PYRIMIDINES AND THEIR USE

RELATED APPLICATIONS

This application is a continuation of U.S. application Ser. No. 13/085,256, filed Apr. 12, 2011. U.S. application Ser. No. 13/085,256 claims the benefit of U.S. Provisional Application Ser. No. 61/323,145, filed Apr. 12, 2010. Each of these applications is incorporated herein by reference in its entirety.

FIELD OF THE INVENTION

The present disclosure relates to the field of nucleic acid chemistry, specifically to 5-position modified uridines as well as phosphoramidites and triphosphates derivatives thereof. The present disclosure also relates to methods of making and using the same. The disclosure includes the use of the modified nucleosides as part of an oligonucleotide or an aptamer.

BACKGROUND

The following description provides a summary of information relevant to the present disclosure and is not an admission that any of the information provided or publications referenced herein is prior art to the present disclosure.

There has been considerable interest in developing modified nucleosides as therapeutic agents, diagnostic agents, and for incorporation into oligonucleotides. For example, modified nucleosides such as AZT, ddI, d4T, and others have been used to treat AIDS. 5-trifluoromethyl-2'-deoxyuridine is active against herpetic keratitis and 5-iodo-1-(2-deoxy-2-fluoro-b-D-arabinofuranosyl)cytosine has activity against CMV, VZV, HSV-1, HSV-2 and EBV (A Textbook of Drug Design and Development, Povl Krogsgaard-Larsen and Hans Bundgaard, Eds., Harwood Academic Publishers, 1991, Ch. 15).

Modified nucleosides have shown utility in diagnostic applications. In these applications, the nucleosides are incorporated into DNA in determinable locations, and various diagnostic methods are used to determine the location of the modified nucleosides. These methods include radiolabeling, fluorescent labeling, biotinylation, and strand cleavage. An example of strand cleavage involves reaction of the nucleoside with hydrazine to yield urea nucleosides, then reaction of the urea nucleoside with piperidine to cause strand cleavage (the Maxam-Gilbert method).

Modified nucleosides have also been incorporated into oligonucleotides. There are several ways in which oligonucleotides may be useful as therapeutics. Antisense oligonucleotides can bind certain genetic coding regions in an organism to prevent the expression of proteins or to block various cell functions. Further, a process known as the SELEX process, or systematic Evolution of Ligands for EXponential Enrichment, allows one to identify and produce oligonucleotides (referred to as "aptamers") that selectively bind target molecules. The SELEX process is described in U.S. Pat. No. 5,270,163, the contents of which are hereby incorporated by reference.

The SELEX method involves the selection of oligonucleotides from a mixture of candidates to achieve virtually any desired criterion of binding affinity and selectivity. Starting from a random mixture of oligonucleotides, the method involves contacting the mixture with a target under conditions favorable for binding (or interacting), partitioning unbound oligonucleotides from oligonucleotides which have bound to (or interacted with) target molecules, dissociating the oligonucleotide-target pairs, amplifying the oligonucleotides dissociated from the oligonucleotide-target pairs to yield a ligand-enriched mixture of oligonucleotides, then reiterating the steps of binding, partitioning, dissociating and amplifying through as many cycles as desired.

Modified nucleosides can be incorporated into antisense oligonucleotides, ribozymes, and oligonucleotides used in or identified by the SELEX process. These nucleosides can impart in vivo and in vitro stability of the oligonucleotides to endo and exonucleases, alter the charge, hydrophilicity or lipophilicity of the molecule, and/or provide differences in three dimensional structure.

Modifications of nucleosides that have been previously described include 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, and methylations. Modifications have also included 3' and 5' modifications such as capping. PCT WO 91/14696, incorporated herein by reference, describes a method for chemically modifying antisense oligonucleotides to enhance entry into a cell.

U.S. Pat. Nos. 5,428,149, 5,591,843, 5,633,361, 5,719,273, and 5,945,527 which are incorporated herein by reference in their entirety, describe modifying pyrimidine nucleosides via palladium coupling reactions. In some embodiments a nucleophile and carbon monoxide are coupled to pyrimidine nucleosides containing a leaving group on the 5-position of the pyrimidine ring, preferably forming ester and amide derivatives.

A variety of methods have been used to render oligonucleotides resistant to degradation by exonucleases. PCT WO 90/15065 describes a method for making exonuclease-resistant oligonucleotides by incorporating two or more phosphoramidite, phosphoromonothionate and/or phosphorodithionate linkages at the 5' and/or 3' ends of the oligonucleotide. PCT WO 91/06629 discloses oligonucleotides with one or more phosphodiester linkages between adjacent nucleosides replaced by forming an acetal/ketal type linkage which is capable of binding RNA or DNA.

It would be advantageous to provide new nucleosides for therapeutic and diagnostic applications and for inclusion in oligonucleotides. When incorporated in oligonucleotides, it would be advantageous to provide new oligonucleotides that exhibit different high affinity binding to target molecules, and/or show increased resistance to exonucleases and endonucleases than oligonucleotides prepared from naturally occurring nucleosides. It would also be useful to provide nucleotides with modifications that impart a biological activity other than, or in addition to, endonuclease and exonuclease resistance.

SUMMARY

The present disclosure provides 5-position modified uridines of the following general formula:

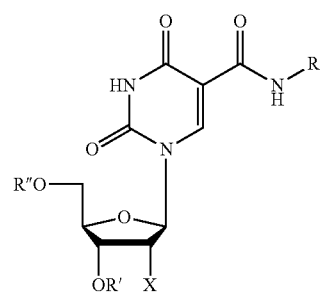

wherein
R is selected from the group consisting of —(CH$_2$)$_n$—R$^{X1}$;
R$^{X1}$ is selected from the group consisting of

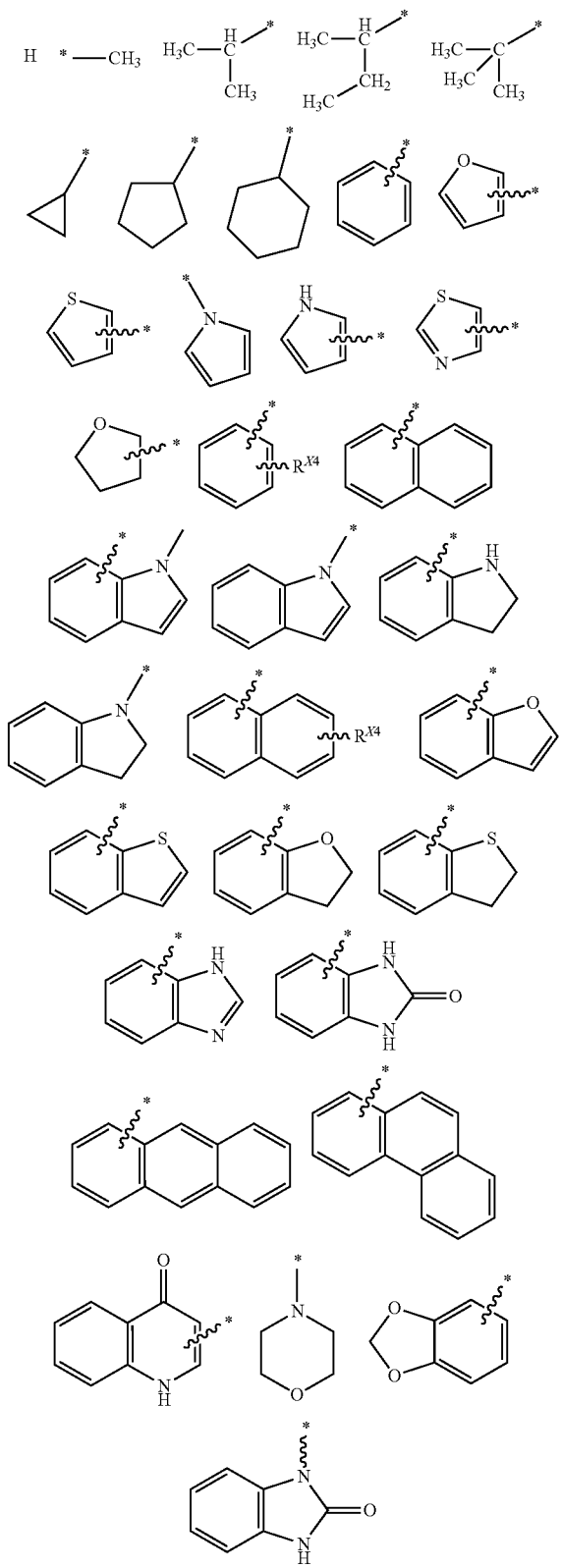

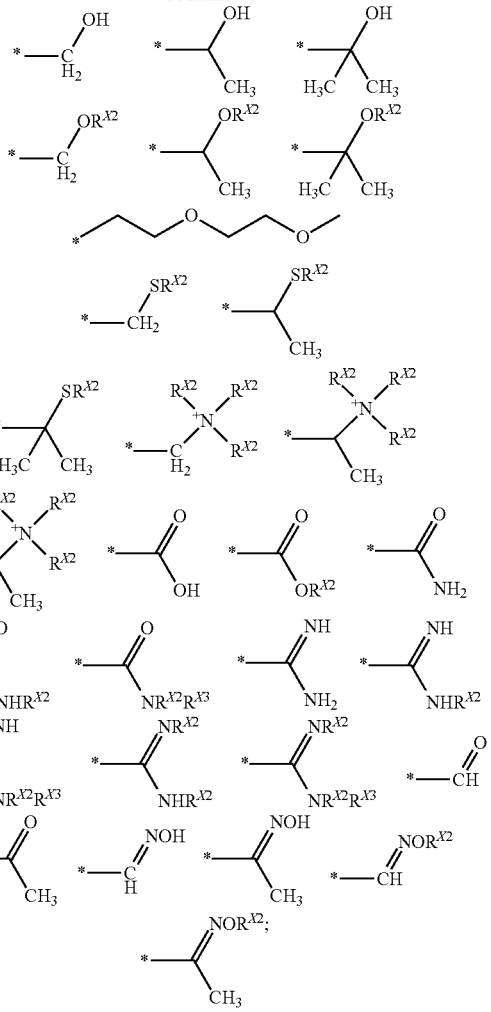

*Denotes point of attachment of the R$^{X1}$ group to (CH$_2$)$_n$ connecting group wherein
R$^{X4}$ is selected from the group consisting of a branched or linear lower alkyl (C1-C20); halogen (F, Cl, Br, I); nitrile (CN); boronic acid (BO$_2$H$_2$); carboxylic acid (COOH); carboxylic acid ester (COOR$^{X2}$); primary amide (CONH$_2$); secondary amide (CONHR$^{X2}$); tertiary amide (CONR$^{X2}$R$^{X3}$); sulfonamide (SO$_2$NH$_2$); N-alkylsulfonamide (SONHR$^{X2}$);
wherein
R$^{X2}$, R$^{X3}$ are independently selected from the group consisting of a branched or linear lower alkyl (C1-C20); phenyl (C$_6$H$_5$); an R$^{X4}$ substituted phenyl ring (R$^{X4}$C$_6$H$_4$), wherein R$^{X4}$ is defined above; a carboxylic acid (COOH); a carboxylic acid ester (COOR$^{X5}$), wherein R$^{X5}$ is a branched or linear lower alkyl (C1-C20); and cycloalkyl, wherein R$^{X2}$=R$^{X3}$=(CH$_2$)n;
wherein n=0-10;
wherein
X is selected from the group including, but not limited to —H, —OH, —OMe, —O-allyl, —F, —OEt, —OPr, —OCH$_2$CH$_2$OCH$_3$ and -azido;
wherein
R' is selected from the group including, but not limited to —OAc; —OBz; and —OSiMe$_2$tBu;

wherein

R" is selected from the group including, but not limited to H, DMT and triphosphate (—P(O)(OH)—O—P(O)(OH)—O—P(O)(OH)$_2$) or a salt thereof; and wherein

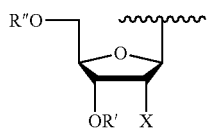

can be replaced with carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

Included are 3'-phosphoramidite and 5'-triphosphate derivatives of said compounds having the following general formulas, respectively or salts thereof:

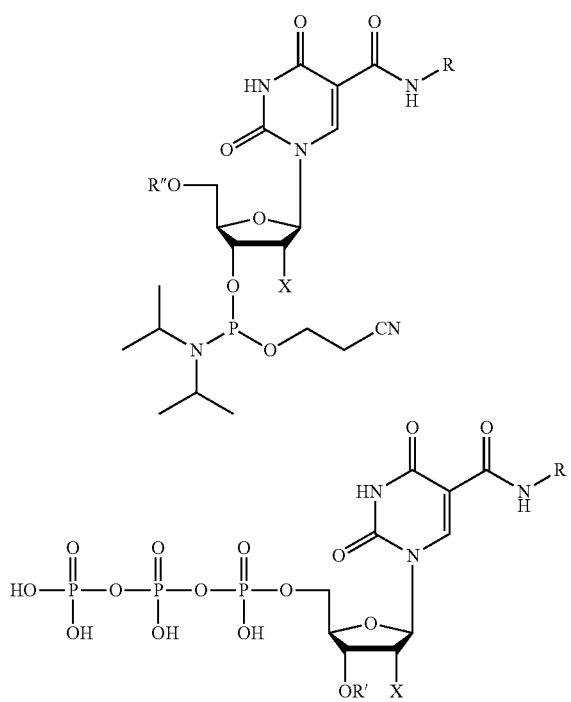

wherein all moieties are as defined above.

The compounds of the present disclosure can be incorporated into oligonucleotides or aptamers using standard synthetic or enzymatic methods of preparing such compounds.

Also provided in the present disclosure are methods for producing the compounds of the present disclosure and the compounds produced by said methods.

In one embodiment, a method is provided for preparing a C-5 modified aminocarbonylpyrimidine said method comprising: reacting a pyrimidine modified at the 5-position with a trifluoroethoxycarbonyl with an amine in the presence of a base; and isolating said C-5 modified aminocarbonylpyrimidine.

In another embodiment, a method is provided for preparing a 3'-phosphoramidite of a C-5 modified aminocarbonylpyrimidine said method comprising: reacting said C-5 modified aminocarbonylpyrimidine with cyanoethyldiisopropyl-chlorophosphoramidite in the presence of a base; and isolating said 3'-phosphoramidite.

In yet another embodiment, a method is provided for preparing a 5'-triphosphate of a C-5 modified aminocarbonylpyrimidine said method comprising:

a) reacting a C-5 modified aminocarbonylpyrimidine having the formula:

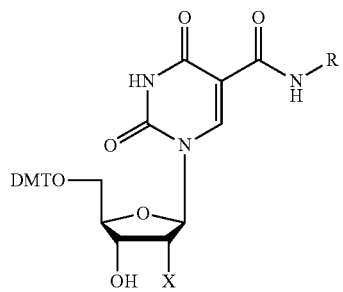

wherein R and X are as defined above, with acetic anhydride in the presence of a base, followed by cleavage of the 5'-DMT group with an acid to form a 3'-acetate of the following structure:

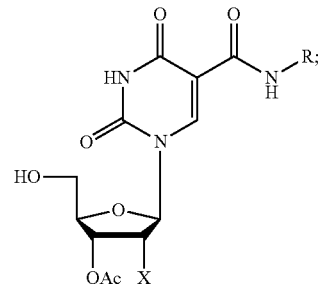

b) performing a Ludwig-Eckstein reaction followed by anion exchange chromatography on the 3'-acetate of step a); and c) isolating a 5'-triphosphate of a C-5 modified aminocarbonylpyrimidine having the following structure or a salt thereof:

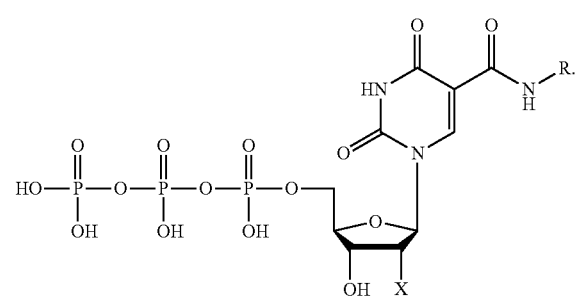

DETAILED DESCRIPTION

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present disclosure. The present disclosure is in no way limited to the methods and materials described.

Unless defined otherwise, technical and scientific terms used herein have the same meaning as commonly understood by one of ordinary skill in the art(s) to which this invention belongs. Although any methods, devices, and materials similar or equivalent to those described herein can be used in the practice or testing of the invention, the preferred methods, devices and materials are now described.

All publications, published patent documents, and patent applications cited in this disclosure are indicative of the level of skill in the art(s) to which the disclosure pertains. All publications, published patent documents, and patent applications cited herein are hereby incorporated by reference to the same extent as though each individual publication, published patent document, or patent application was specifically and individually indicated as being incorporated by reference.

As used in this disclosure, including the appended claims, the singular forms "a," "an," and "the" include plural references, unless the content clearly dictates otherwise, and are used interchangeably with "at least one" and "one or more." Thus, reference to "an aptamer" includes mixtures of aptamers, and the like.

As used herein, the term "about" represents an insignificant modification or variation of the numerical value such that the basic function of the item to which the numerical value relates is unchanged.

The term "each" when used herein to refer to a plurality of items is intended to refer to at least two of the items. It need not require that all of the items forming the plurality satisfy an associated additional limitation.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs).

Compounds

In one embodiment, the present disclosure provides compounds of the following formula:

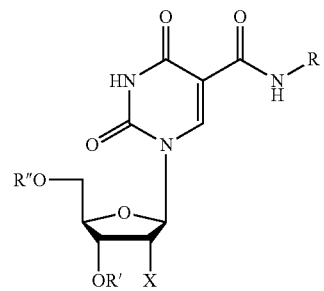

wherein
R is selected from the group consisting of —$(CH_2)_n$—$R^{X1}$;
$R^{X1}$ is selected from the group consisting of

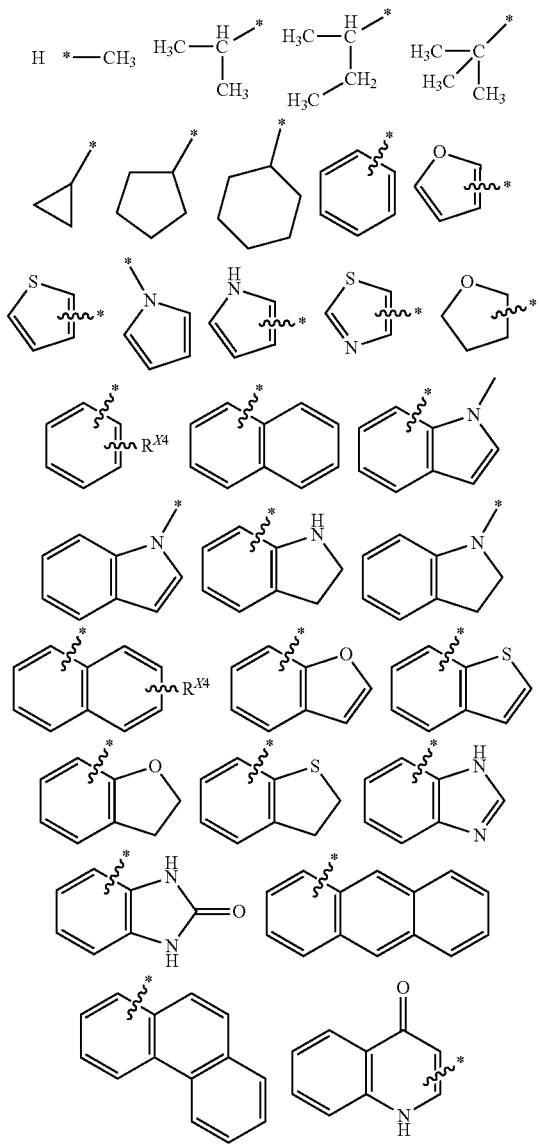

-continued

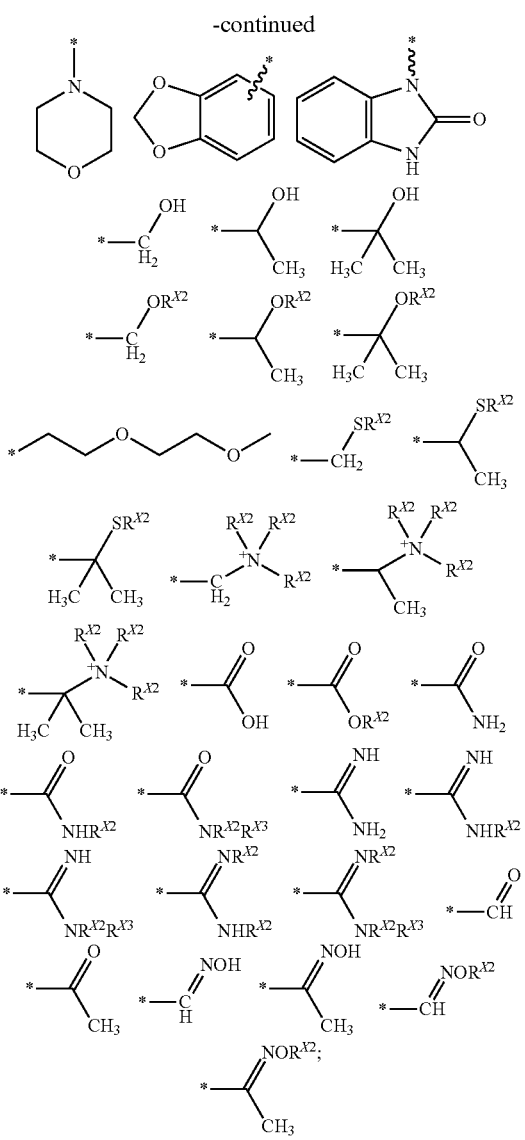

*Denotes point of attachment of the $R^{X1}$ group to $(CH_2)_n$ connecting group wherein
$R^{X4}$ is selected from the group including, but not limited to, a branched or linear lower alkyl (C1-C20); halogen (F, Cl, Br, I); nitrile (CN); boronic acid ($BO_2H_2$); carboxylic acid (COOH); carboxylic acid ester ($COOR^{X2}$); primary amide ($CONH_2$); secondary amide ($CONHR^{X2}$); tertiary amide ($CONR^{X2}R^{X3}$); sulfonamide ($SO_2NH_2$); and N-alkylsulfonamide ($SONHR^{X2}$);
wherein
$R^{X2}$, $R^{X3}$ are independently selected from the group including, but not limited to a branched or linear lower alkyl (C1-C20); phenyl ($C_6H_5$); an $R^{X4}$ substituted phenyl ring ($R^{X4}C_6H_4$), wherein $R^{X4}$ is defined above; a carboxylic acid (COOH); a carboxylic acid ester ($COOR^{X5}$), wherein $R^{X5}$ is a branched or linear lower alkyl (C1-C20); and cycloalkyl, wherein $R^{X2}=R^{X3}=(CH_2)n$;
wherein n=0-10;
wherein
X is selected from the group including, but not limited to —H, —OH, —OMe, —O-allyl, —F, —OEt, —OPr, —OCH$_2$CH$_2$OCH$_3$ and -azido;

wherein
R' is selected from the group including, but not limited to —H, —Ac, -Bz, —C(O)CH$_2$OCH$_3$, and —SiMe$_2$tBu;
wherein
R" is selected from the group including, but not limited to —H, 4,4'-dimethoxytrityl (DMT), and triphosphate (—P(O)(OH)—O—P(O)(OH)—O—P(O)(OH)$_2$) or a salt thereof; and;
wherein

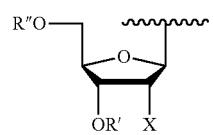

can be replaced with carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

In another embodiment, the present disclosure provides compounds of the following formula or salts thereof:

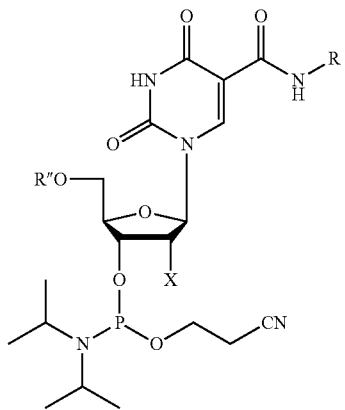

wherein R, R" and X are as defined above. Compounds of this general formula are useful for incorporation of the modified nucleoside into an oligonucleotide by chemical synthesis.

In yet other embodiments, the present disclosure provides compounds of the formula or salts thereof:

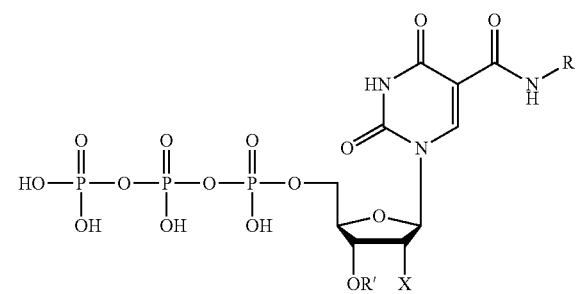

wherein R, R' and X are as defined above. Compounds of this general formula are useful for incorporation of the modified nucleoside into an oligonucleotide by enzymatic synthesis.

As used herein, the term "C-5 modified carboxyamideuridine" or "C-5 modified aminocarbonyluridine" refers to a uridine with a carboxyamide (—C(O)NH—) modification at the C-5 position of the uridine including, but not limited to, those moieties (R) illustrated above. Examples of a C-5 modified carboxyamideuridines include those described in U.S. Pat. Nos. 5,719,273 and 5,945,527, as well as, U.S. Provisional Application Ser. No. 61/422,957 (the '957 application), filed Dec. 14, 2010, entitled "Nuclease Resistant Oligonucleotides." Representative C-5 modified pyrimidines include: 5-(N-benzylcarboxyamide)-2'-deoxyuridine (BndU), 5-(N-benzylcarboxyamide)-2'-β-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine or 5-(N-[1-(2,3-dihydroxypropyl)]carboxyamide)-2'-deoxyuridine).

Specific examples of C-5 modified aminocarbonyluridines, described herein for purposes of illustration only, include the following compounds as well as the 5'-triphosphates and 3'-phosphoramidites and salts thereof of said compounds, the syntheses of which are described in Examples 1-5.

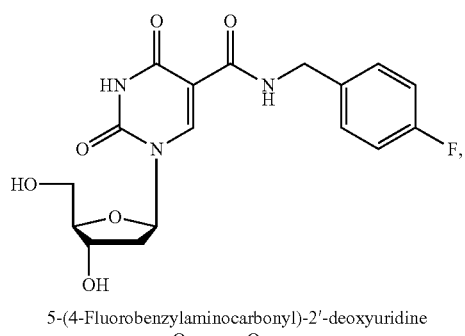

5-(4-Fluorobenzylaminocarbonyl)-2'-deoxyuridine

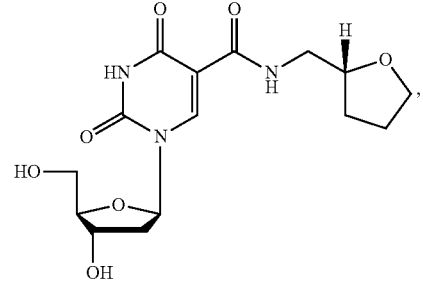

5-((R)-2-Furfurylmethylaminocarbonyl)-2'-deoxyuridine

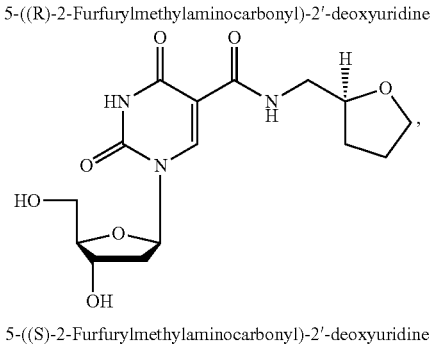

5-((S)-2-Furfurylmethylaminocarbonyl)-2'-deoxyuridine

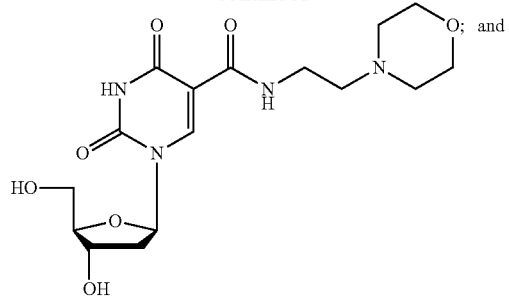

5-(2-(4-Morpholino)ethylaminocarbonyl)-2'-deoxyuridine

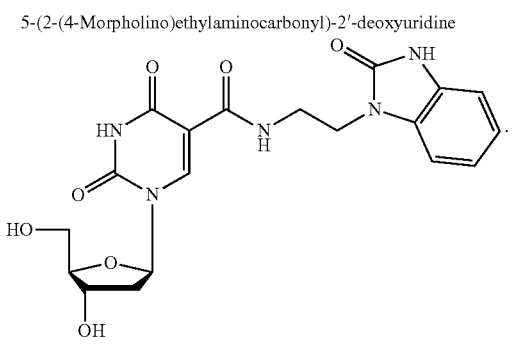

5-(2-(1-benzimidazolonyl)ethylaminocarbonyl)-2'-deoxyuridine

Chemical modifications of the C-5 modified uridines described herein can also be combined with, singly or in any combination, 2'-position sugar modifications, modifications at exocyclic amines, and substitution of 4-thiouridine and the like.

Salts

It may be convenient or desirable to prepare, purify, and/or handle a corresponding salt of the compound, for example, a pharmaceutically-acceptable salt. Examples of pharmaceutically acceptable salts are discussed in Berge et al. "Pharmaceutically Acceptable Salts" (1977) J. Pharm. Sci. 66:1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^{x+}$, $NH_2R^x{}_2^+$, $NHR^x{}_3^+$, $NR^x{}_4^+$). Examples of some suitable substituted ammonium ions are those derived from: ethylamine, diethylamine, dicyclohexylamine, triethylamine, butylamine, ethylenediamine, ethanolamine, diethanolamine, piperizine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Preparation of Oligonucleotides

In one aspect, the instant disclosure provides methods for using the modified nucleosides described herein, either alone or in combination with other modified nucleosides and/or naturally occurring nucleosides, to prepare modified oligonucleotides. The automated synthesis of oligodeoxynucleosides is routine practice in many laboratories (see e.g., Matteucci, M. D. and Caruthers, M. H., (1990) J. Am. Chem. Soc., 103:3185-3191, the contents of which are hereby incorporated by reference). Synthesis of oligoribonucleosides is also well known (see e.g. Scaringe, S. A., et al., Nucleic Acids Res. 18:5433-5441 (1990), hereby incorporated by reference). As noted above, the phosphoramidites are useful for incorporation of the modified nucleoside into an oligonucleotide by chemical synthesis, and the triphosphates are useful for incorporation of the modified nucleoside into an oligonucleotide by enzymatic synthesis. (See e.g., Vaught, J. V., et al. (2010) J. Am. Chem. Soc., 132, 4141-4151; Gait, M. J. "Oligonucleotide Synthesis a practical approach" (1984) IRL Press (Oxford, UK); Herdewijn, P. "Oligonucleotide Synthesis" (2005) (Humana Press, Totowa, N.J. (each of which is incorporated herein by reference in its entirety).

As used herein, the terms "modify," "modified," "modification," and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. Additional modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers.

Polynucleotides can also contain analogous forms of ribose or deoxyribose sugars that are generally known in the art, including 2'-O-methyl, 2'-O-allyl, 2'-O-ethyl, 2'-O-propyl, 2'-O—$CH_2CH_2OCH_3$, 2'-fluoro- or 2'-azido, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)$NR^x_2$ ("amidate"), P(O) $R^x$, P(O) $OR^{x'}$, CO or $CH_2$ ("formacetal"), in which each $R^x$ or $R^{x'}$ are independently H or substituted or unsubstituted alkyl (C1-C20) optionally containing an ether (—O—) linkage, aryl, alkenyl, cycloalkyl, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

If present, a modification to the nucleotide structure can be imparted before or after assembly of a polymer. A sequence of nucleotides can be interrupted by non-nucleotide components. A polynucleotide can be further modified after polymerization, such as by conjugation with a labeling component.

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

As used herein, the term "at least one nucleotide" when referring to modifications of a nucleic acid, refers to one, several, or all nucleotides in the nucleic acid, indicating that any or all occurrences of any or all of A, C, T, G or U in a nucleic acid may be modified or not.

In other aspects, the instant disclosure methods for using the modified nucleosides described herein, either alone or in combination with other modified nucleosides and/or naturally occurring nucleosides, to prepare aptamers and SOMAmers (described below). In specific embodiments, the aptamers and SOMAmers are prepared using the general SELEX or improved SELEX process as described below.

As used herein, "nucleic acid ligand," "aptamer," "SOMAmer," and "clone" are used interchangeably to refer to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure other than a polynucleotide that binds to the nucleic acid ligand through a mechanism which is independent of Watson/Crick base pairing or triple helix formation, wherein the aptamer is not a nucleic acid having the known physiological function of being bound by the target molecule. Aptamers to a given target include nucleic acids that are identified from a candidate mixture of nucleic acids, where the aptamer is a ligand of the target, by a method comprising: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby aptamers of the target molecule are identified. It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample. An "aptamer," "SOMAmer," or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers can have either the same or different numbers of nucleotides. Aptamers may be DNA or RNA and may be single stranded, double stranded, or contain double stranded or triple stranded regions.

As used herein, a "SOMAmer" or Slow Off-Rate Modified Aptamer refers to an aptamer having improved off-rate characteristics. SOMAmers can be generated using the improved SELEX methods described in U.S. Publication No. 20090004667, entitled "Method for Generating Aptamers with Improved Off-Rates.".

As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

The SELEX Method

The terms "SELEX" and "SELEX process" are used interchangeably herein to refer generally to a combination of (1) the selection of nucleic acids that interact with a target molecule in a desirable manner, for example binding with high affinity to a protein, with (2) the amplification of those selected nucleic acids. The SELEX process can be used to identify aptamers with high affinity to a specific target molecule or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands." The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH$_2$), 2'-fluoro (2'-F), and/or 2'-O-methyl (2'-OMe). See also, U.S. Patent Application Publication No. 20090098549, entitled "SELEX and PHOTOSELEX," which describes nucleic acid libraries having expanded physical and chemical properties and their use in SELEX and photoSELEX.

SELEX can also be used to identify aptamers that have desirable off-rate characteristics. See U.S. Patent Publication No. 20090004667, entitled "Method for Generating Aptamers with Improved Off-Rates," which is incorporated herein by reference in its entirety, describes improved SELEX methods for generating aptamers that can bind to target molecules. Methods for producing aptamers and photoaptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates dissociate and do not reform, while complexes with slow dissociation rates remain intact. Additionally, the methods include the use of modified nucleotides in the production of candidate nucleic acid mixtures to generate aptamers with improved off-rate performance (see U.S. Patent Publication No. 20090098549, entitled "SELEX and PhotoSELEX"). (See also U.S. Pat. No. 7,855,054 and U.S. Patent Publication No. 20070166740). Each of these applications is incorporated herein by reference in its entirety.

"Target" or "target molecule" or "target" refers herein to any compound upon which a nucleic acid can act in a desirable manner. A target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. Virtually any chemical or biological effector may be a suitable target. Molecules of any size can serve as targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Embodiments of the SELEX process in which the target is a peptide are described in U.S. Pat. No. 6,376,190, entitled "Modified SELEX Processes Without Purified Protein."

Chemical Synthesis

Methods for the chemical synthesis of compounds provided in the present disclosure are described herein. These and/or other well-known methods may be modified and/or adapted in known ways in order to facilitate the synthesis of additional compounds provided in the present disclosure.

With reference to Scheme 1, in one approach the C-5 position modified aminocarbonylpyrimidines of the instant disclosure are prepared by reacting a pyrimidine modified at the 5-position with a trifluoroethoxycarbonyl with an amine in the presence of a base; and isolating said C-5 modified aminocarbonylpyrimidine.

In some embodiments, the trifluoroethoxycarbonylpyrimidine is selected from the group of compounds including, but not limited to compounds having the following structure:

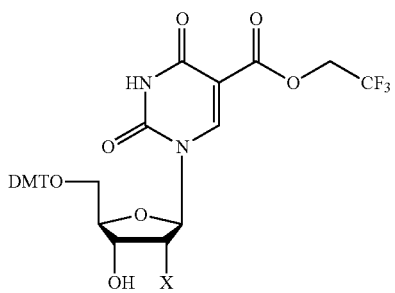

wherein

X is selected from the group including, but not limited to —H, —OH, —OMe, —O-allyl, —F, —OEt, —OPr, —OCH$_2$CH$_2$OCH$_3$ and -azido, and wherein

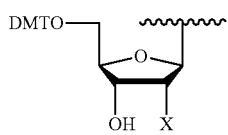

can be replaced with carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

In some embodiments, the amine is selected from the group including, but not limited to compounds of the formula RNH$_2$, wherein R is selected from the group consisting of —(CH$_2$)$_n$—R$^{X1}$;

R$^{X1}$ is selected from the group consisting of:

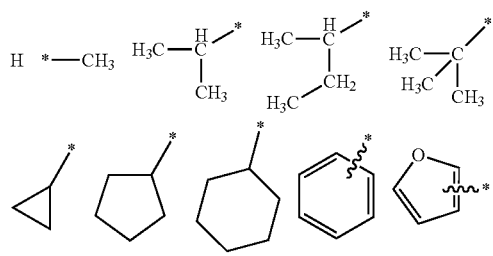

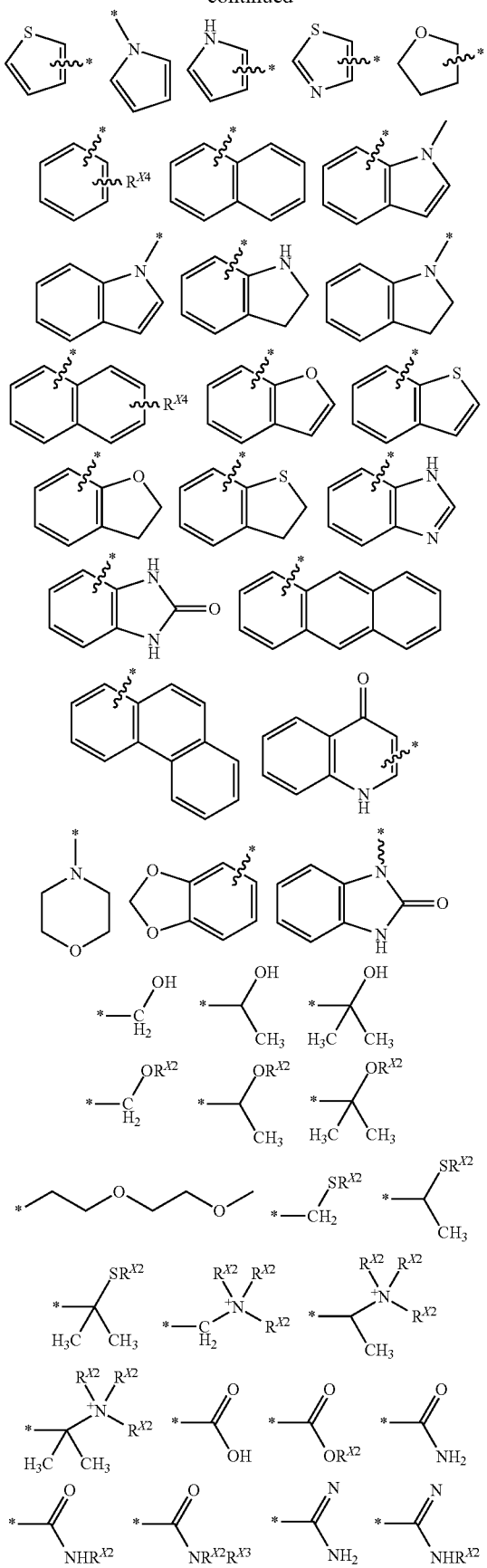

-continued

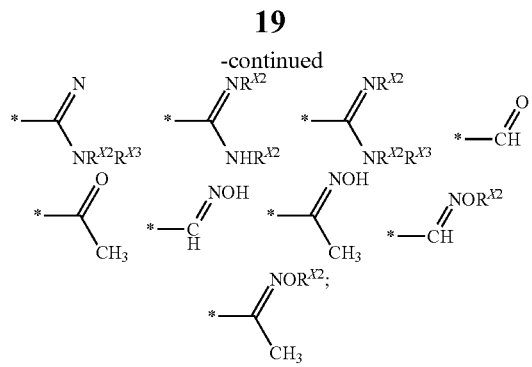

*Denotes point of attachment of the $R^{X1}$ group to $(CH_2)_n$ connecting group wherein $R^{X4}$ is selected from the group consisting of a branched or linear lower alkyl (C1-C20); halogen (F, Cl, Br, I); nitrile (CN); boronic acid ($BO_2H_2$); carboxylic acid (COOH); carboxylic acid ester ($COOR^{X2}$); primary amide ($CONH_2$); secondary amide ($CONHR^{X2}$); tertiary amide ($CONR^{X2}R^{X3}$); sulfonamide ($SO_2NH_2$); N-alkylsulfonamide ($SONHR^{X2}$);

wherein $R^{X2}$ and $R^{X3}$ are independently selected from the group consisting of a branched or linear lower alkyl (C1-C20); phenyl ($C_6H_5$); an $R^{X4}$ substituted phenyl ring ($R^{X4}C_6H_4$), wherein $R^{X4}$ is defined above; a carboxylic acid (COOH); a carboxylic acid ester ($COOR^{X5}$), wherein $R^{X5}$ is a branched or linear lower alkyl (C1-C20); and cycloalkyl, wherein $R^{X2}=R^{X3}=(CH_2)_n$; and wherein n=0-10.

In specific embodiments, the amine is selected from the group consisting of:

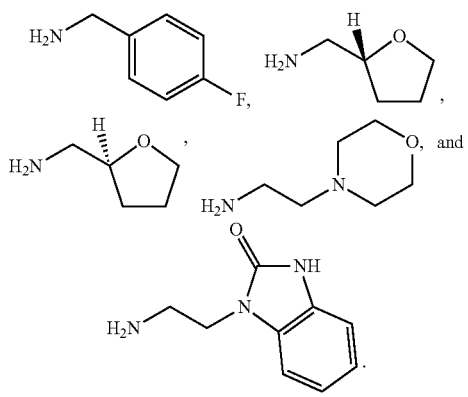

In some embodiments the base is a tertiary amine selected from the group consisting of triethylamine, diisopropylamine and the like.

With reference to Scheme 1, the present disclosure also provides a method for the synthesis of a 3'-phosphoramidite of a C-5 modified aminocarbonylpyrimidine comprising: reacting said C-5 modified aminocarbonylpyrimidine with cyanoethyldiisopropyl-chlorophosphoramidite in the presence of a base; and isolating said 3'-phosphoramidite. In some embodiments the C-5 modified aminocarbonylpyrimidine has the following structure:

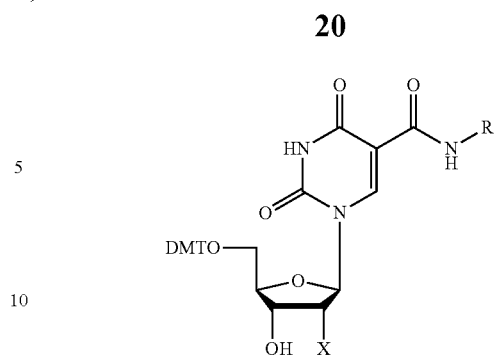

wherein R and X are as defined above. In some embodiments, the base is a tertiary amine selected from the group consisting of consisting of triethylamine, diisopropylamine and the like.

Again with reference to Scheme 1, the present disclosure also provides a method for the synthesis of a 5'-triphosphate of a C-5 modified aminocarbonylpyrimidine comprising:

a) reacting a C-5 modified aminocarbonylpyrimidine having the formula:

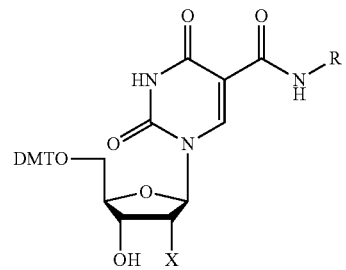

wherein R and X are as defined above, with acetic anhydride in the presence of a base, followed by cleavage of the 5'-DMT group with an acid to form a 3'-acetate of the following structure:

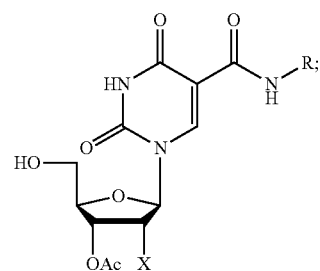

b) performing a Ludwig-Eckstein reaction followed by anion exchange chromatography on the 3'-acetate of step a); and c) isolating a 5'-triphosphate of a C-5 modified aminocarbonylpyrimidine having the following structure or a salt thereof:

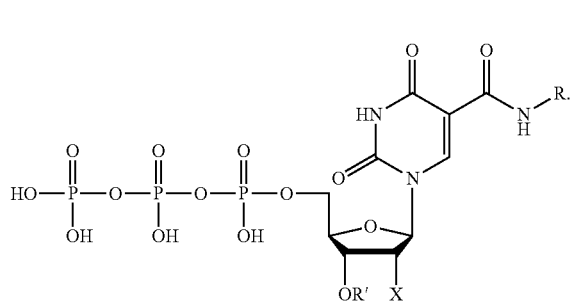

The base used is selected from the group including, but not limited to a tertiary amine. In some embodiments the base is pyridine. The acid used in step a is selected from the group including, but not limited to dichloroacetic acid, trichloroacetic acid and 1,1,1,3,3,3-hexafluoro-2-propanol.

In an alternate approach, the trifluoroethoxycarbonylpyrimidine has the following structure:

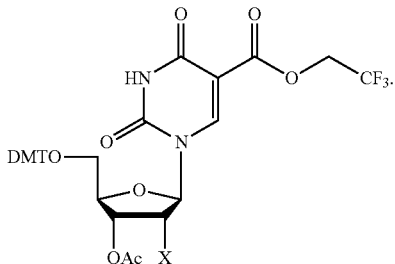

With reference to Scheme 2, this compound is formed by the reaction of compound (7) of Scheme 2 with carbon monoxide and trifluoroethanol in the presence of a palladium catalyst and a base. The base is selected from the group including, but not limited to a tertiary amine selected from triethylamine and the like.

The present disclosure includes compounds prepared by each of the above described methods.

EXAMPLES

The following examples are provided for illustrative purposes only and are not intended to limit the scope of the invention as defined by the appended claims. All examples described herein were carried out using standard techniques, which are well known and routine to those of skill in the art. Routine molecular biology techniques described in the following examples can be carried out as described in standard laboratory manuals, such as Sambrook et al., Molecular Cloning: A Laboratory Manual, 3rd. ed., Cold Spring Harbor Laboratory Press, Cold Spring Harbor, N.Y., (2001).

The following general procedures were employed to produce the modified nucleosides described in Examples 1-3 and 5. The nomenclature used herein is based upon the system described by Matsuda et al. Nucleic Acids Research 1997, 25:2784-2791.

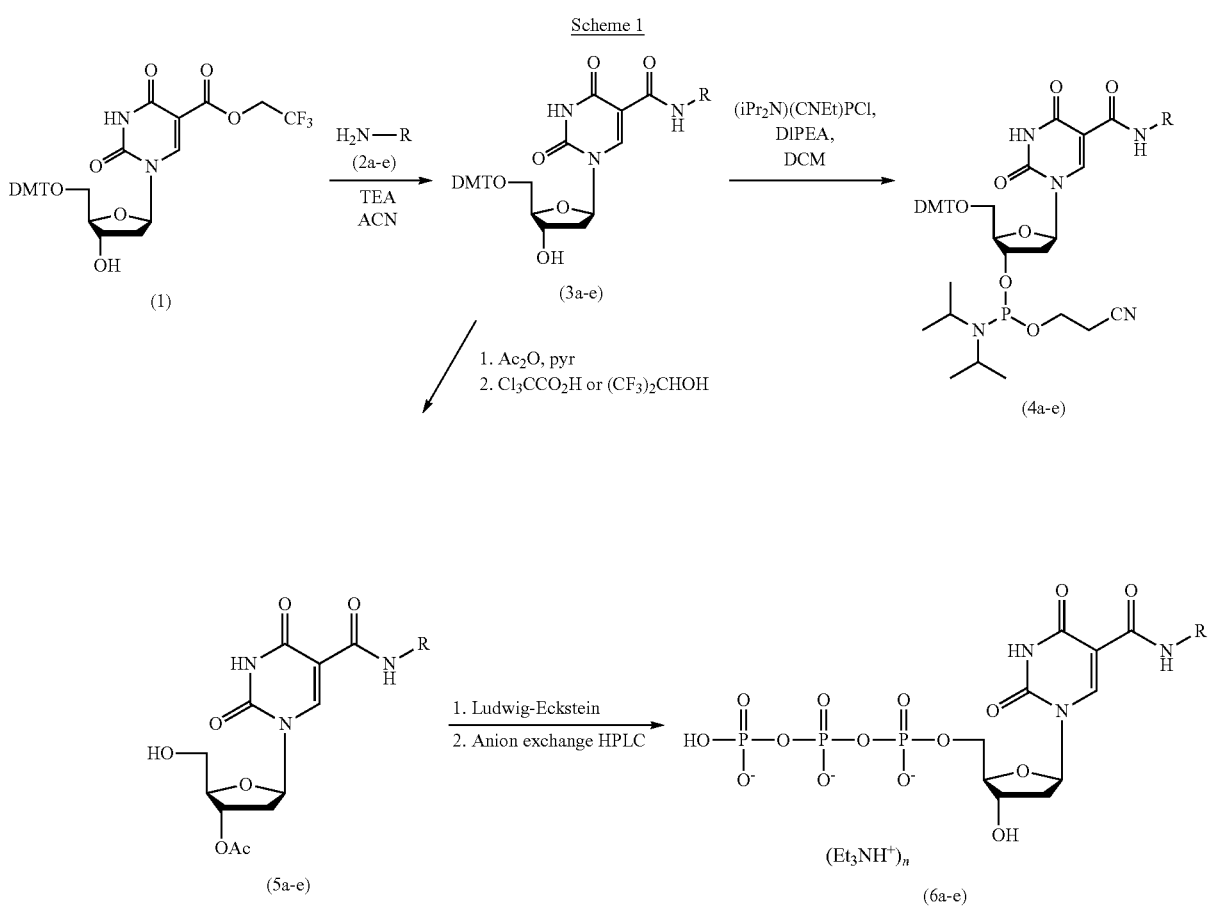

Scheme 1

R =

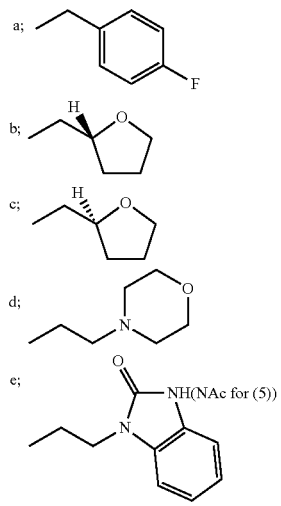

a;
b;
c;
d;
e; NH(NAc for (5))

Example 1

Synthesis of 5'-O-DMT-dU-5-Carboxamides (3a-e)

5'-O-Dimethoxytrityl-5-(4-fluorobenzylaminocarbonyl)-2'-deoxyuridine (3a). The starting material, 5'-O-dimethoxytrityl-5-trifluoroethoxycarbonyl-2'-deoxyuridine (1) was prepared by the procedure of Matsuda et al (Nomura, Y.; Ueno, Y.; Matsuda, A. *Nucleic Acids Research* 1997, 25:2784-2791; Ito, T., Ueno, Y.; Matsuda, A. *Nucleic Acids Research* 2003, 31:2514-2523). A solution of (1) (9.85 g, 15 mmol), 4-fluorobenzylamine (2a) (2.25 g, 18 mmol, 1.3 eq), triethylamine (4.2 mL, 30 mmol), and anhydrous acetonitrile (30 mL) was heated under an inert atmosphere at 60-70° C. for 2-24 hours. Quantitative conversion of (1) to amide (3a) was confirmed by thin layer chromatography (silica gel 60, 5% methanol/dichloromethane) or HPLC. The reaction mixture was concentrated in vacuo and the residue purified by silica gel flash chromatography (Still, W. C.; Kahn, M.; Mitra, A. *J. Org. Chem.* 1978, 43:2923) using an eluent of 0-3% methanol in 1% triethylamine/99% ethyl acetate. Fractions containing pure product were combined and evaporated. Traces of residual solvents were removed by co-evaporation with anhydrous acetonitrile, followed by drying under high vacuum, to afford (3a) as a white solid (6.57 g, 64% yield). $^1$H-NMR (300 MHz, CD$_3$CN) δ 2.20-2.40 (2H, m), 3.28 (2H, d, J=4.3 Hz), 3.76 (6H, s), 4.01 (1 H, dd, J=3.8, 4.2 Hz), 4.26-4.30 (1 H, m), 4.48 (2H, bd, J=6.1 Hz), 6.11 (1H, t, J=6.5 Hz), 6.85-7.46 (13H, m), 7.03-7.36 (4 H, m), 8.58 (1 H, s), 9.01 (1H, t, J=6.1 Hz). MS (m/z) calcd for C$_{38}$H$_{36}$FN$_3$O$_8$, 681.25; found 680.4 [M-H]$^-$.

5'-O-Dimethoxytrityl-5-((R)-2-furfurylmethylaminocarbonyl)-2'-deoxyuridine (3b). The compound (3b) was prepared as described for (3a) using (R)-2-furfurylmethylamine (2b) and isolated as a white solid (9.3 g, 94% yield). The eluent for chromatography was 1% triethylamine/4% methanol/95% ethyl acetate. $^1$H-NMR (CD$_3$CN) δ 1.51-1.57 (1H, m), 1.84-1.94 (3H, m), 2.18-2.38 (2H, m), 3.25-3.52 (4H, m overlap), 3.66-3.93 (3H, m overlap), 3.78 (6H, s), 3.97-4.02 (1H, m), 4.24-4.29 (1H, m), 6.12 (1 H, t, J=6.5), 6.86-7.47 (13H, m), 8.54 (1H, s), 8.83 (1H, bs). MS (m/z) calcd for C$_{36}$H$_{39}$N$_3$O$_9$, 657.27; found 656.5 [M-H]$^-$.

5'-O-Dimethoxytrityl-5-((S)-2-furfurylmethylaminocarbonyl)-2'-deoxyuridine (3c). The compound (3c) was prepared as described for (3b) using (S)-2-furfurylmethylamine (2c) and isolated as a white solid (9.9 g, 99% yield). $^1$H-NMR (CD$_3$CN) δ 1.50-1.59 (1H, m), 1.84-1.95 (3H, m), 2.18-2.40 (2H, m), 3.24-3.50 (4H, m overlap), 3.69-3.97 (3H, m overlap), 3.78 (6H, s), 3.98-4.02 (1H, m), 4.25-4.30 (1H, m), 6.14 (1 H, t, J=6.5), 6.87-7.47 (13H, m), 8.54 (1H, s), 8.84 (1H, bs). MS (m/z) calcd for C$_{36}$H$_{39}$N$_3$O$_9$, 657.27; found 656.5 [M-H]$^-$.

5'-O-Dimethoxytrityl-5-(2-(4-morpholino)ethylaminocarbonyl)-2'-deoxyuridine (3d). The compound (3d) was prepared as described for (3a), using 2-(4-morpholino)-ethylamine (2d), and isolated as a white solid (8.2 g, 80% yield). The eluent for chromatography was 5% methanol/2% triethylamine/93% dichloromethane. $^1$H-NMR (CD$_3$CN) δ 2.21-2.39 (2H, m), 2.39-2.41 (4H, m), 2.48 (2H, t, J=6.2 Hz), 3.27-3.29 (2H, m), 3.41 (2H, dt, J=5.8, 6.2 Hz), 3.61-3.64 (4H, m), 3.78 (6H, s), 3.98-4.02 (1H, m), 4.25-4.30 (1H, m), 6.10 (1H, t, J=6.4), 6.86-7.47 (13H, m), 8.55 (1H, s), 8.79 (1H, bt, J~6 Hz). MS (m/z) calcd for C$_{37}$H$_{42}$N$_4$O$_9$, 686.30; found 685.7 [M-H]$^-$.

5'-O-Dimethoxytrityl-5-(2-(N-benzimidazolonyl)ethylaminocarbonyl)-2'-deoxyuridine (3e). The compound (3e) was prepared as described for (3a) using N-benzimidazolonyl-2-ethylamine (2e) (CAS RN64928-88-7). The eluent for chromatography was 2% methanol/1% triethylamine/97% dichloromethane. The pure product was isolated as a tan solid (8.2 g, 74.5% yield). $^1$H-NMR (CD$_3$CN) δ 2.20-2.36 (2H, m), 3.27-3.29 (2H, m), 3.60 (2H, q, J=6.5 Hz), 3.758 (3H, s), 3.762 (3H, s), 3.97 (2H, t, J=6.5 Hz), 3.98-4.02 (1H, m), 4.27-4.30 (1H, m), 6.09 (1H, t, J=6.5 Hz), 6.86-7.48 (13H, m), 6.91-7.10 (4H, m), 8.52 (1H, s), 8.76 (1H, t, J=6.1 Hz). MS (m/z) calcd for C$_{40}$H$_{39}$N$_5$O$_9$, 733.27; found 732.0 [M-H]$^-$.

Example 2

Synthesis of 5'-O-DMT-nucleoside CE-phosphoramidites (4a-4e)

5'-O-Dimethoxytrityl-5-(4-fluorobenzylaminocarbonyl)-3'-O-[(2-cyanoethyl)(N,N-diisopropylamino)phosphinyl]-2'-deoxyuridine (4a). A solution of DMT-protected nucleoside (3a) (4.00 g, 5.9 mmol) in anhydrous dichloromethane (40 mL) was cooled to approximately −10° C. under an atmosphere of dry argon. Diisopropylethylamine (3.1 mL, 17.6 mmol, 3 eq) was added, followed by dropwise addition of 2-cyanoethyldiisopropylchlorophosphoramidite (1.7 mL, 7.7 mmol, 1.3 eq). The solution was stirred for one hour and complete reaction was confirmed by thin layer chromatography (silica gel 60, ethyl acetate/hexane). The reaction mixture was partitioned between ice-cold 2% sodium bicarbonate solution (200 mL) and ethyl acetate (200 mL). The organic layer was washed with brine, dried over anhydrous sodium sulfate, filtered, and concentrated. The residue was purified by silica gel flash chromography using a mobile phase of 1% triethylamine/99% ethyl acetate. Fractions containing pure product were combined and evaporated in vacuo (<30° C.). Traces of residual chromatography solvent were removed by co-evaporation with anhydrous acetonitrile and drying at high vacuum to afford (4a) as a white solid foam (4.10 g, 80% yield). $^1$H-NMR (CD$_3$CN, two isomers) δ 1.02-1.16 (12H, m), 2.27-2.57 (2H, m), 2.51/2.62 (2H, 2t, J=6.0/6.0 Hz), 3.25-3.37 (2H, m), 3.50-3.79 (4H, m overlap), 3.738 (3H, s), 3.742 (3H, s), 4.13/4.16 (1H, 2q, J=3.5/3.7 Hz), 4.37-4.43 (1H, m), 4.44-4.47 (2H, m), 6.09/6.10 (1H, 2t, J=6.4/7.1 Hz), 6.83-7.44 (13H, m), 7.01-7.30 (4H, m), 8.58/8.60 (1H, 2s), 8.98 (1H, b, J~5.5 Hz), 9.24 (1H, bs). $^{31}$P-NMR (CD$_3$CN) δ 148.01 (s), 148.06 (s). $^{19}$F-NMR (CD$_3$CN) δ −117.65 (m). MS (m/z) calcd for C$_{47}$H$_{53}$FN$_5$O$_9$P, 881.36; found 880.3 [M-H]$^-$.

5'-O-Dimethoxytrityl-5-((R)-2-furfurylmethylaminocarbonyl)-3'-O-[(2-cyanoethyl)(N,N-diisopropylamino)phosphinyl]-2'-deoxyuridine (4b). The compound (4b) was prepared as described for (4a). A 1:1 mixture of diastereomeric phosphoramidites was isolated as a white solid foam (3.15 g, 62% yield). The eluent for chromatography was 1% treithylamine/20% hexanes/79% ethyl acetate. $^1$H-NMR (CD$_3$CN, two isomers) δ 1.14-1.27 (12H, m), 1.51-1.59 (1H, m), 1.86-1.94 (3H, m), 2.27-2.59 (2H, m), 2.54/2.65 (2H, 2t, J=6.0/5.7 Hz), 3.27-3.38 (2H, m), 3.44-3.97 (9H, m overlap), 3.782 (3H, s), 3.786 (3H, s), 4.11-4.18 (1H, m), 4.39-4.48 (1H, m), 6.11/6.13 (1H, 2t, J=5.6/6.1 Hz), 6.96-7.47 (13H, m), 8.58/8.60 (1H, 2s), 8.75 (1 H, bt, J~5.4 Hz), 9.36 (1H, bs). $^{31}$P-NMR (CD$_3$CN) δ 148.09 (s), 148.13 (s). MS (m/z) calcd for C$_{45}$H$_{56}$N$_5$O$_{10}$P, 857.38; found 856.6 [M-H]$^-$.

5'-O-Dimethoxytrityl-5-((S)-2-furfurylmethylaminocarbonyl)-3'-O-[(2-cyanoethyl)(N,N-diisopropylamino)phosphinyl]-2'-deoxyuridine (4c). The compound (4c) was prepared as described for (4b). A 1:1 mixture of diastereomeric phosphoramidites was isolated as a white solid foam (3.74 g, 74% yield). $^1$H-NMR (CD$_3$CN, two isomers) δ 1.14-1.27 (12H, m), 1.51-1.59 (1H, m), 1.86-1.94 (3H, m), 2.28-2.51 (2H, m), 2.53/2.65 (2H, 2t, J=6.0/6.0 Hz), 3.25-3.41 (2H, m), 3.44-4.14 (9H, m overlap), 3.783 (3H, s), 3.786 (3H, s), 4.12-4.19 (1H, m), 4.40-4.49 (1H, m), 6.11/6.13 (1H, 2t, J=6.3/6.3 Hz), 6.86-7.48 (13H, m), 8.58/8.60 (1H, 2s), 8.75 (1 H, bt, J~5.4 Hz), 9.36 (1H, bs). $^{31}$P-NMR (CD$_3$CN) δ 148.09 (s), 148.13 (s). MS (m/z) calcd for C$_{45}$H$_{56}$N$_5$O$_{10}$P, 857.38; found 856.5 [M-H]$^-$.

5'-O-Dimethoxytrityl-5-(2-(4-morpholino)ethylaminocarbonyl)-3'-O-[(2-cyanoethyl)(N,N-diisopropylamino)phosphinyl]-2'-deoxyuridine (4d). The compound (4d) was prepared as described for (4a) except that the purification used a chromatography eluent of 1% triethylamine/5% anhydrous ethanol/94% ethyl acetate. The 1:1 mixture of diastereoisomeric phosphoramidites was isolated as a white solid foam (3.9 g, 75% yield). $^1$H-NMR (CD$_3$CN, two isomers) δ 1.04-1.19 (12H, m), 2.28-2.59 (2H, m), 2.43-2.47 (6H, m overlap), 2.53/2.64 (2H, 2t, J=6.2/6.2 Hz), 3.27-3.76 (8H, m overlap), 3.61-3.65 (4H, m), 3.781 (3H, s), 3.789 (3H, s), 4.12-4.19 (1H, m), 4.39-4.49 (1H, m), 6.11/6.13 (1H, 2t, J=5.2//5.2), 6.86-7.48 (13H, m), 8.58/8.60 (1H, 2s), 8.78 (1H, bt, J~5.3 Hz), 9.78 (1H, bs). $^{31}$P-NMR (CD$_3$CN) δ 148.08 (s), 148.11 (s). MS (m/z) calcd for C$_{46}$H$_{59}$N$_6$O$_{10}$P, 886.4; found 885.7 [M-H]$^-$.

5'-O-Dimethoxytrityl-5-(2-(N-benzimidazolonyl)ethylaminocarbonyl)-3'-O-[(2-cyanoethyl)(N,N-diisopropylamino)phosphinyl]-2'-deoxyuridine (4e). The compound (4e) was prepared as described for (4a) except that the purification used a chromatography eluent of 1% triethylamine/10% anhydrous methanol/89% ethyl acetate. The 1:1 mixture of diastereomeric phosphoramidites was isolated as a white solid foam (1.6 g, 31% yield). $^1$H-NMR (CD$_3$CN, two isomers) δ 1.03-1.18 (12H, m), 2.27-2.57 (2H, m), 2.52/2.63 (2H, 2t, J=6.0/6.0), 3.27-3.37 (2H, m), 3.49-3.80 (6H, m overlap), 3.732 (3H, s), 3.735/3.738 (3H, 2s), 4.00 (2H, bt, J~6.0 Hz), 4.12-4.18 (1H, m), 4.30-4.47 (1H, m), 6.08/6.10 (1H, 2t, J=6.3/6.3 Hz), 6.85-7.48 (13H, m), 6.93-7.09 (4H, m), 8.57/8.60 (1H, 2s), 8.82/8.83 (1H, 2bt, J~4.3/4.3 Hz), 9.48 (1H, bs). $^{31}$P-NMR (CD$_3$CN) δ 148.07 (s), 148.10 (s).

Example 3

Synthesis of 3'-O-Acetyl-Nucleosides (5a-5e)

5-(4-Fluorobenzylaminocarbonyl)-3'-O-acetyl-2'-deoxyuridine (5a)

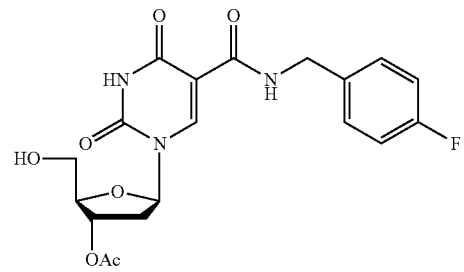

5a

The nucleoside (3a) (3.00 g, 4.4 mmol) was dissolved in a solution of anhydrous pyridine (30 mL) and acetic anhydride (3 mL). The solution was stirred overnight and concentrated in vacuo to yield the 3'-O-acetyl-nucleoside. Residual solvent was removed by co-evaporation with anhydrous toluene (10 mL). The residue was dissolved in anhydrous dichloromethane (10 mL) and treated with 3% trichloroacetic acid in dichloromethane (58 mL). The red solution was stirred overnight, during which time the product crystallized. The slurry was cooled to −20° C., filtered, and washed with diethyl ether. The residue was dried in vacuo to afford (5a) as an off-white solid (1.10 g, 59% yield). $^1$H-NMR (CD$_3$CN) δ 2.07 (3H, s), 2.33-2.38 (1H, m), 2.50-2.52 (1H, m), 3.63-3.64 (2H, m), 4.10 (1H, bdd, J=3.1, 5.1 Hz), 4.46 (2H, d, J=6.0 Hz), 5.19-5.26 (2 H, m overlap), 6.15 (1H, t, J=7.0 Hz), 7.15 (2H, tt, J=2.2, 9.0 Hz), 7.31-7.38 (2H, m), 8.79 (1H, s), 9.14 (1H, bt, J=6.1 Hz), 11.95 (1H, bs). $^{19}$F-NMR (CD$_3$CN) δ −116.02 (tt, J=5.5, 9.0 Hz)). MS (m/z) calcd for C$_{19}$H$_{20}$FN$_3$O$_7$, 421.13; found 419.8 [M-H]$^-$.

5-((R)-2-Furfurylmethylaminocarbonyl)-3'-O-acetyl-2'-deoxyuridine (5b)

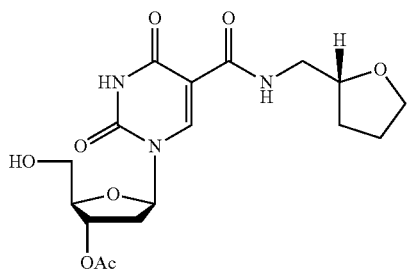

The compound (5b) was prepared from (4b), by the procedure described for (5a) and isolated by precipitation from a mixture of dichloromethane and ethyl acetate as a white solid (1.27 g, 73% yield). $^1$H-NMR (CDCl$_3$) δ 1.57-2.02 (4H, m), 2.12 (3H, s), 2.46-2.50 (2H, m), 3.03 (1H, bs), 3.43-3.64 (2H, m), 3.75-3.97 (2H, m), 3.78-4.10 (3H, m), 4.20-4.21 (1H, m), 5.40-5.42 (1H, m), 6.35 (1H, dd, J=6.5, 7.7 Hz), 8.91 (1H, t, J=5.5 Hz), 9.17 (1H, s), 9.44 (1H, bs). MS (m/z) calcd for C$_{17}$H$_{23}$N$_3$O$_8$, 397.15; found 396.1 [M-H]$^-$.

5-((S)-2-Furfurylmethylaminocarbonyl)-3'-O-acetyl-2'-deoxyuridine (5c)

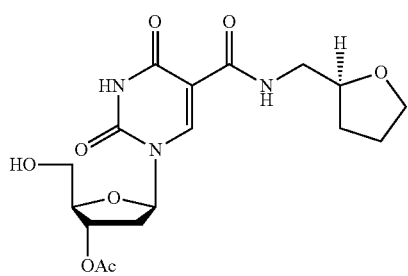

The compound (5c) was prepared from (4c), by the procedure described for (5a), and isolated by precipitation from a mixture of dichloromethane and diethyl ether as a slightly orange solid (1.35 g, 77% yield). $^1$H-NMR (CDCl$_3$) δ 1.57-2.03 (4H, m), 2.12 (3H, s), 2.47-2.51 (2H, m), 2.98 (1H, bs), 3.40-3.68 (2H, m), 3.78-3.95 (2H, m), 3.90-4.12 (3H, m), 4.20-4.21 (1H, m), 5.39-5.42 (1H, m), 6.33 (1H, dd, J=6.7, 7.4 Hz), 8.90 (1H, t, J=5.5 Hz), 9.15 (1H, s), 9.37 (1H, bs). MS (m/z) calcd for C$_{17}$H$_{23}$N$_3$O$_8$, 397.15; found 395.9 [M-H]$^-$.

5-(2-(4-Morpholino)ethylaminocarbonyl)-3'-O-acetyl-2'-deoxyuridine (5d)

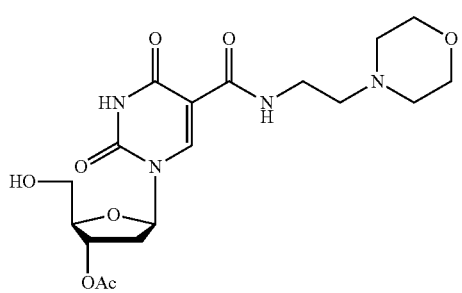

The nucleoside (3d) (1.00 g, 1.37 mmol) was dissolved in a solution of anhydrous pyridine (10 mL) and acetic anhydride (1 mL). The solution was stirred overnight and concentrated in vacuo to yield the 3'-O-acetyl-nucleoside. Residual solvent was removed by coevaporation with anhydrous toluene (10 mL). The residue was dissolved in 1,1,1,3,3,3-hexafluoro-2-propanol (20 mL) (Leonard, N.J. Tetrahedron Letters, 1995, 36:7833) and heated at approximately 50° C. for 3 hours. Complete cleavage of the DMT group was confirmed by tlc. The red solution mixture was quenched by pouring into well-stirred methanol (200 mL). The resulting yellow solution was concentrated in vacuo and the residue was dissolved in hot ethyl acetate (20 mL). The product crystallized upon cooling and the resulting slurry was aged at −20° C., followed by filtration and washing with ethyl acetate. The 3'-O-acetyl-nucleoside (5d) was isolated as a white solid (0.46 g, 79% yield). $^1$H-NMR (DMSO-d6) δ 2.07 (3H, s), 2.32-2.45 (7H, m overlap), 2.49-2.52 (1H, m), 3.33-3.40 (2H, m), 3.57 (4H, t, J=4.5 Hz), 3.60-3.63 (2H, m), 4.09 (1H, bdd, J=3.2, 5.2 Hz), 5.17-5.25 (2H, m), 6.14 (1H, t, J=7.0 Hz), 8.74 (1H, s), 8.89 (1H, bt, J=5.4 Hz), 11.90 (1H, bs). MS (m/z) calcd for C$_{18}$H$_{26}$N$_4$O$_8$, 426.18; found 425.0 [M-H]$^-$.

5-(2-(1-(3-Acetyl-benzimidazolonyl))ethylaminocarbonyl)-3'-O-acetyl-2'-deoxyuridine (5e)

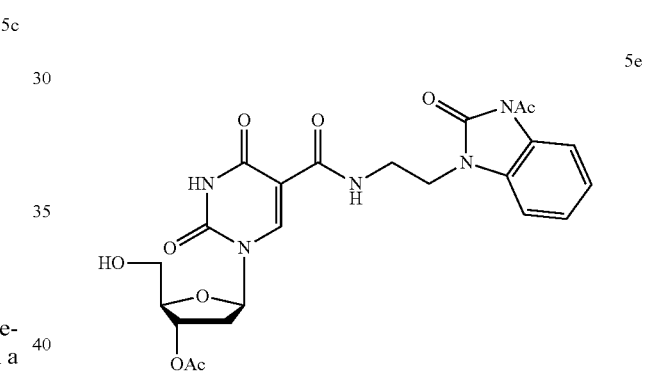

The compound (5e) was prepared as described for (5d) except that the product crystallized directly when the DMT-cleavage reaction was poured into methanol. The diacetyl nucleoside (5e) was isolated by filtration as a white solid (0.55 g, 78% yield). $^1$H-NMR (DMSO-d6) δ 2.07 (3H, s), 2.30-2.37 (1H, m), 2.49-2.52 (1H, m), 2.63 (3H, s) 3.33 (1H, bs), 3.55-3.64 (4H, m overlap), 3.99 (2H, t, J=6.4 Hz), 4.09 (1H, bdd, J=2.3, 5.2 Hz), 5.15-5.25 (2H, m), 6.13 (1H, dd, J=6.3, 7.6 Hz), 7.11 (1H, ddd, J=1.2, 7.6, 7.9 Hz), 7.22 (1H, ddd, J=1.2, 7.6, 7.9 Hz), 7.33 (1H, dd, J=0.8, 7.9 Hz), 8.02 (1H, dd, J=0.8, 8.0 Hz), 8.05 (1H, bs), 8.83 (1H, bt), 8.71 (1H, s), 11.87 (1H, bs). MS (m/z) calcd for C$_{23}$H$_{25}$N$_5$O$_9$, 515.17; found 513.9 [M-H]$^-$.

Example 4

Alternative synthesis of 3'-O-Acetyl-Nucleosides (5a-5d)

The 3'-O-acetyl-nucleosides (5a-d) were also synthesized by an alternative route (Scheme 2) from the starting material, 3'-O-acetyl-5'-O-dimethoxytrityl-5-iodo-2'-deoxyuridine (7) (Vaught, J. D., Bock, C., Carter, J., Fitzwater, T., Otis, M., Schneider, D., Rolando, J., Waugh, S., Wilcox, S. K., Eaton, B. E. J. Am. Chem. Soc. 2010, 132, 4141-4151). Briefly, with reference to Scheme 2, palladium(II)-catalyzed rifluoroethoxycarbonylation of the iodide afforded the activated ester intermediate (8). Condensation of (8) with the amines (2a-d) (1.3 eq., triethylamine (3 eq), acetonitrile, 60-70° C., 2-24 hours), followed by cleavage of the 5'-O-DMT-protecting group (3% trichloroacetic acid/dichloromethane or 1,1,1,3,3,3-hexafluoro-2-propanol, room temperature), afforded (5a-d), identical to the products produced via intermediates (3a-d) (Scheme 1).

Scheme 2

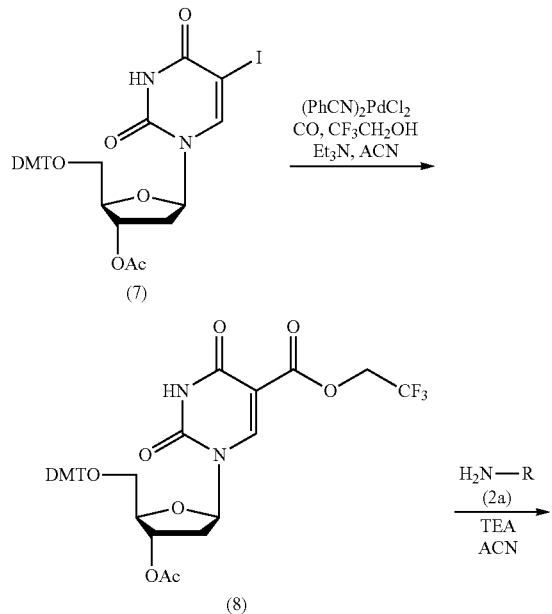

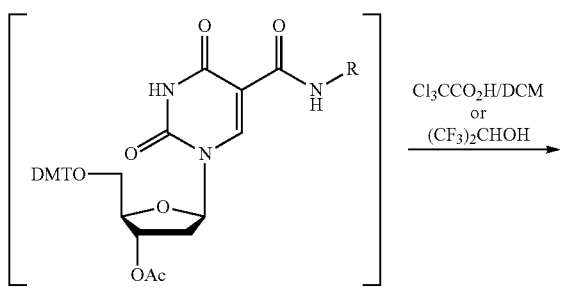

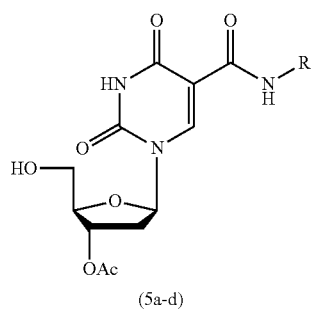

R =

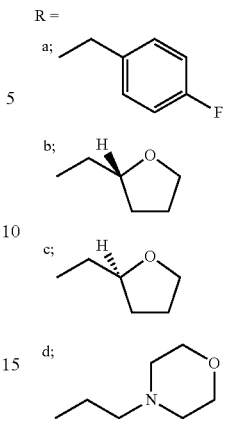

3'-O-Acetyl-5'-O-dimethoxytrityl-5-(2,2,2-trifluoroethoxycarbonyl)-2'-deoxyuridine (8). A 500 mL heavy-walled glass pressure reactor was filled with argon and charged with 3'-O-acetyl-5'-O-dimethoxytrityl-5-iodo-2'-deoxyuridine (7) (15.9 g, 22.8 mmol), anhydrous acetonitrile (200 mL), triethylamine (7.6 mL, 54.7 mmol), and 2,2,2-trifluoroethanol (16.4 mL, 228 mmol). The resulting solution was vigorously stirred and degassed by evacuation to <100 mmHg for 2 minutes. The flask was filled with argon and bis(benzonitrile)dichloropalladium(II) (175 mg, 0.46 mmol) was added. The resulting yellow solution was again degassed and then filled with carbon monoxide (99.9%) (Caution Poison Gas!) from a gas manifold. A pressure of 1-10 psi CO was maintained while the reaction mixture was vigorously stirred and heated at 60-65 degC for 12 hours. The cooled reaction mixture was filtered (Caution Poison Gas) to remove black precipitate and concentrated in vacuo. The orange residue was partitioned with dichloromethane (120 mL) and 10% sodium bicarbonate (80 mL). The organic layer was washed with water (40 mL) and dried over sodium sulfate, filtered, and concentrated to leave a orange foam (17 g). This crude product could be used as is or further purified by silica gel flash chromatography with an eluent of 30% hexane/1% triethylamine/69% ethyl acetate to afford (8) as a colorless solid foam (12.7 g, 80% yield). $^1$H-NMR (CD$_3$CN)) δ 2.03 (3H, s), 2.37-2.56 (2H, m), 3.36-3.38 (2H, m), 3.78 (6H, s), 4.15-4.19 (1H, m), 4.37-4.55 (2H, m), 5.21-5.26 (1H, m), 6.09 (1H, t, J=6.1 Hz), 6.84-7.46 (13H, m), 8.53 (1H, s). $^{19}$F-NMR (CD$_3$CN) δ −74.07 (t, J=8.8 Hz). MS (m/z) calcd for $C_{35}H_{33}F_3N_2O_{10}$, 698.21; found 697.4 [M-H]$^−$.

Example 5

Synthesis of Nucleoside 5'-O-Triphosphates 5-(4-Fluorobenzylaminocarbonyl)-2'-deoxyuridine-5'-O-triphosphate (tris-triethylammonium salt) (6a). The triphosphate (6a) was synthesized from the 3'-O-acetyl-nucleoside (5a) by the procedure of Ludwig and Eckstein (Ludwig, J. and Eckstein, F. *J. Org. Chem.* 1989, 54:631) at 500 μmol-scale (5×). The crude triphosphate product, after ammonolysis and evaporation, was purified by anion exchange chromatography, as described in the General Procedure (below).

General Procedure for Anion Exchange HPLC Purification of Nucleoside Triphosphates. Nucleoside triphosphates were purified via anion exchange chromatography using an HPLC column packed with Source Q resin (GE Healthcare), installed on a preparative HPLC system, with detection at 278 nm. The linear elution gradient employed two buffers, (buffer A: 10 mM triethylammonium bicarbonate/10% acetonitrile, and buffer B: 1 M triethylammonium bicarbonate/10% acetonitrile), with the gradient running at ambient temperature from low buffer B content to high buffer B over the course of the elution. The desired product was typically the final material to elute from the column and was observed as a broad peak spanning approximately ten to twelve minutes retention time (early eluting products included a variety of reaction by-products, the most significant being the nucleoside diphosphate). Several fractions were collected during product elution. Fraction was analyzed by reversed phase HPLC on a Waters 2795 HPLC with a Waters Symmetry column (PN: WAT054215). Pure product-containing fractions (typically >90%) were evaporated in a Genevac VC 3000D evaporator to afford colorless to light tan resins. Fractions were reconstituted in deionized water and pooled for final analysis. Product quantitation was performed by analysis using a Hewlett Packard 8452A Diode Array Spectrophotometer at 278 nm. Product yields were calculated via the equation $A=\epsilon CL$, where A is the UV absorbance, $\epsilon$ is the estimated extinction coefficient and L is the pathlength (1 cm).

The crude product (6a) was dissolved in approximately 5 mL of buffer A (Table 1: prep-HPLC Conditions 1). Each purification injection consisted of a filtered aliquot of approximately 1 mL of this solution injected into a Waters 625 HPLC with a 486 detector fitted with a Resource Q 6 mL column (GE Healthcare product code: 17-1179-01) with a mobile phase gradient of 0%-100% buffer B in a 50 minute elution at 12 mL/minute. For (6a) [$\epsilon_{est.}$ 13,700 cm$^{-1}$ M$^{-1}$] the isolated purified product was 130 µmol (26% yield). $^1$H-NMR (D$_2$O) δ 1.15 (27H, t, J=7.3 Hz), 2.32-2.37 (2H, m), 3.07 (18H, q, J=7.3 Hz), 4.06-4.17 (3H, m overlap), 4.42 (2H, bd, J~0.7 Hz), 4.49-4.53 (1H, m), 4.70 (>7H, bs, HOD), 6.12 (1H, t, J=6.8 Hz), 6.96-7.26 (4H, m), 8.45 (1H, s). $^{19}$F-NMR (D$_2$O) δ −116.18 (m). $^{31}$P-NMR (D$_2$O) δ −10.58 (d, J=20 Hz), −11.45 (d, J=20 Hz), −23.29 (t, J=20 Hz). MS (m/z) calcd for C$_{17}$H$_{21}$FN$_3$O$_{15}$P$_3$, 619.02; found 618.0 [M-H]$^-$.

TABLE 1

| | Prep-HPLC Conditions 1 |
|---|---|
| Mobile Phase | A: 10 mM triethylammonium bicarbonate/10% acetonitrile |
| | B: 1M triethylammonium bicarbonate/10% acetonitrile |
| Column | Resource Q 6 mL |
| HPLC system | Waters 625HPLC/486 detector |
| Gradient (% Buffer B in mobile phase) | 0%-100% |
| Run Time/flow rate | 50 minutes at 12 mL/minute |

5-((R)-2-Furfurylmethylaminocarbonyl)-2'-deoxyuridine-5'-β-triphosphate (tris-triethylammonium salt) (6b). The triphosphate (6b) was synthesized from the 3'-O-acetyl-nucleoside (5b) as described for (6a). The crude product (6b) was purified in a single injection on a Waters 2767 preparatory system with a Waters 2489 detector using a Waters AP-5 column (Waters PN: WAT023331, 50 mm×100 mm) packed with 196 mL of Source 15Q resin (GE Healthcare product code: 17-0947-05). The same buffers as above were used, but the elution gradient was modified to 25% to 80% buffer B in a 90 minute elution at 50 mL/minute (Table 2: prep-HPLC Conditions 2). A second purification was performed on a C18 HPLC column to remove residual impurities (Table 4: prep-HPLC Conditions 4). For (6b) [$\epsilon_{est.}$ 10,200 cm$^{-1}$ M$^{-1}$] the isolated purified product was 325 µmol (65% yield). $^1$H-NMR (D$_2$O) δ 1.17 (27H, t, J=7.3 Hz), 1.49-1.63 (1H, m), 1.77-2.02 (3H, m), 2.34-2.39 (2H, m), 2.85-3.83 (5H, m overlap), 3.08 (18H, q, J=7.3 Hz), 4.01-4.19 (3H, m overlap), 4.52-4.56 (1H, m), 4.70 (>7H, bs, HOD), 6.15 (1H, t, J=6.8 Hz), 8.48 (1H, s). $^{31}$P-NMR (D$_2$O) δ −10.50 (d, J=20 Hz), −11.51 (d, J=20 Hz), −23.25 (t, J=20 Hz). MS (m/z) calcd for C$_{15}$H$_{24}$FN$_3$O$_{16}$P$_3$, 595.04; found 594.1 [M-H]$^-$.

TABLE 2

| | Prep-HPLC Conditions 2 |
|---|---|
| Mobile Phase | A: 10 mM triethylammonium bicarbonate/10% acetonitrile |
| | B: 1M triethylammonium bicarbonate/10% acetonitrile |
| Column | Resource Q 6 mL |
| HPLC system | Waters 625HPLC/486 detector |
| Gradient (% Buffer B in mobile phase) | 15%-60% |
| Run Time/flow rate | 50 minutes at 12 mL/minute |

5-((S)-2-Furfurylmethylaminocarbonyl)-2'-deoxyuridine-5'-β-triphosphate (tris-triethylammonium salt) (6c). The triphosphate (6c) was synthesized from the 3'-O-acetyl-nucleoside (5c) as described for (6a). The crude product (6c) was purified in a single injection on a Waters 2767 preparatory system with a Waters 2489 detector using a Waters AP-5 column (Waters PN: WAT023331, 50 mm×100 mm) packed with 196 mL of Source 15Q resin (GE Healthcare product code: 17-0947-05). The same buffers as above were used, but the elution gradient was modified to 25% to 80% buffer B in a 90 minute elution at 50 mL/minute (Table 2: prep-HPLC Conditions 2). A second purification was performed on a C18 HPLC column to remove residual impurities (Table 4: prep-HPLC Conditions 4). For (6c) [$\epsilon_{est.}$ 10,200 cm$^{-1}$ M$^{-1}$] the isolated purified product was 255 µmol (51% yield). $^1$H-NMR (D$_2$O) δ 1.17 (27H, t, J=7.3 Hz), 1.49-1.63 (1H, m), 1.78-2.01 (3H, m), 2.34-2.39 (2H, m), 2.85-3.82 (5H, m overlap), 3.09 (18H, q, J=7.3 Hz), 4.01-4.19 (3H, m overlap), 4.52-4.56 (1H, m), 4.70 (>7H, bs, HOD), 6.15 (1H, t, J=6.7 Hz), 8.48 (1H, s). $^{31}$P-NMR (D$_2$O) δ −10.60 (d, J=20 Hz), −11.42 (d, J=20 Hz), −23.25 (t, J=20 Hz). MS (m/z) calcd for C$_{15}$H$_{24}$FN$_3$O$_{16}$P$_3$, 595.04; found 594.1 [M-H]$^-$.

5-(2-(4-Morpholino)ethylaminocarbonyl)-2'-deoxyuridine-5'-β-triphosphate (bis-triethylammonium salt) (6d). The triphosphate (6d) was synthesized from the 3'-O-acetyl-nucleoside (5d) as described for (6a). The crude product (6d) was purified with the same equipment and buffers as used for (6a), but the gradient was modified to run buffer B from 15% to 60% during the 50 minute elution to improve resolution of products (Table 3: prep-HPLC Conditions 3). For (6d) [$\epsilon_{est.}$ 10,200 cm$^{-1}$ M$^{-1}$] the isolated purified product was 54 µmol (11% yield). $^1$H-NMR (D$_2$O) δ 1.17 (18H, t, J=7.3 Hz), 2.37-2.41 (2H, m), 2.91-2.98 (2H, m), 3.09 (12H, q, J=7.3 Hz), 3.20-3.27 (4H, m), 3.87-3.90 (4H, m), 3.63-3.68 (2H, m), 4.10-4.18 (3H, m overlap), 4.56-4.60 (1H, m), 4.70 (>7H, bs, HOD), 6.15 (1H, bt, J=6.3 Hz), 8.48 (1H, s). $^{31}$P-NMR (D$_2$O) δ −9.99 (d, J=21 Hz), −11.90 (d, J=20 Hz), −23.19 (t, J=20 Hz). MS (m/z) calcd for C$_{16}$H$_{27}$N$_4$O$_{16}$P$_3$, 624.06; found 623.1 [M-H]$^-$.

TABLE 3

| Prep-HPLC Conditions 3 | |
|---|---|
| Mobile Phase | A: 10 mM triethylammonium bicarbonate/10% acetonitrile |
| | B: 1M triethylammonium bicarbonate/10% acetonitrile |
| Column | Waters AP-5 with Source Q 196 mL |
| HPLC system | Waters 22767HPLC/2489 detector |
| Gradient (% Buffer B in mobile phase) | 25-80% |
| Run Time/flow rate | 90 minutes at 50 mL/minute |

TABLE 4

| Prep-HPLC Conditions 4 | |
|---|---|
| Mobile Phase | A: 100 mM triethylammonium B: acetonitrile |
| Column | Waters Novapk C18, 19 mm × 300 mm |
| HPLC system | Waters 625HPLC/486 detector |
| Gradient (% Buffer B in mobile phase) | 10-25% |
| Run Time/flow rate | 30 minutes at 8.5 mL/minute |

5-(2-(N-Benzimidazolonyl)ethylaminocarbonyl)-2'-deoxyuridine-5'-β-triphosphate (bis-triethylammonium salt) (6e). The triphosphate (6e) was synthesized from the 3'-O-acetyl-nucleoside (5e) as described for (6a). The crude product (6e) was purified with the same equipment and buffers as used for (6a), but the gradient was modified to run buffer B from 15% to 60% during the 50 minute elution to improve resolution of products (Table 3: prep-HPLC Conditions 3). For (6e) [$\epsilon_{est.}$ 13,700 cm$^{-1}$ M$^{-1}$] the isolated purified product was 101 μmol (20% yield). $^1$H-NMR (D$_2$O) δ 1.17 (18H, t, J=7.3 Hz), 2.17-2.36 (2H, m), 3.09 (12H, q, J=7.3 Hz), 3.60-3.73 (2H, m), 4.01 (2H, t, J=5.4 Hz), 4.03-4.15 (3H, m), 4.45-4.50 (1H, m), 4.70 (>7H, bs, HOD), 6.04 (1H, t, J=6.6 Hz), 6.95-7.12 (4H, m), 8.02 (1H, s). $^{31}$P-NMR (D$_2$O) δ −10.35 (d, J=20 Hz), −11.40 (d, J=20 Hz), −23.23 (t, J=20 Hz). MS (m/z) calcd for C$_{19}$H$_{24}$N$_5$O$_{16}$P$_3$, 671.04; found 670.1 [M-H]$^-$.

The foregoing embodiments and examples are intended only as examples. No particular embodiment, example, or element of a particular embodiment or example is to be construed as a critical, required, or essential element or feature of any of the claims. Further, no element described herein is required for the practice of the appended claims unless expressly described as "essential" or "critical." Various alterations, modifications, substitutions, and other variations can be made to the disclosed embodiments without departing from the scope of the present invention, which is defined by the appended claims. The specification, including the examples, is to be regarded in an illustrative manner, rather than a restrictive one, and all such modifications and substitutions are intended to be included within the scope of the invention. Accordingly, the scope of the invention should be determined by the appended claims and their legal equivalents, rather than by the examples given above. For example, steps recited in any of the method or process claims may be executed in any feasible order and are not limited to an order presented in any of the embodiments, the examples, or the claims.

What is claimed is:

1. A C-5 modified aminocarbonylpyrimidine having the following structure:

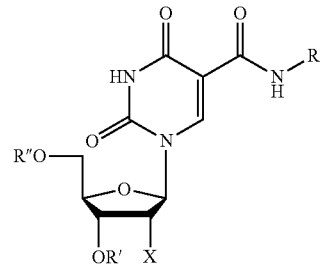

wherein

R' is selected from the group consisting of —H, —Ac, —Bz, —CH$_2$CH$_2$OCH$_3$, —C(O)CH$_2$OCH$_3$, and —SiMe$_2$tBu;

R" is selected from the group consisting fo H, DMT and triphosphate (—P(O)(OH)—O—P(O)(OH)—O—P(O)(OH)$_2$) or a salt thereof;

X is selected from the group consisting of —H, —OH, —OMe, —O-allyl, —F, —OEt, —OPr, —OCH$_2$CH$_2$OCH$_3$ and -azido;

R is selected from the group consisting of —(CH$_2$)$_n$—R$^{X1}$;

R$^{X1}$ is selected from the group consisting of:

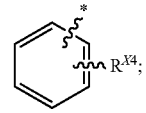

R$^{X4}$ is; and n=0–10.

2. A 3'-phosporamidite of a C-5 modified aminocarbonylpyrimidine having the following structure:

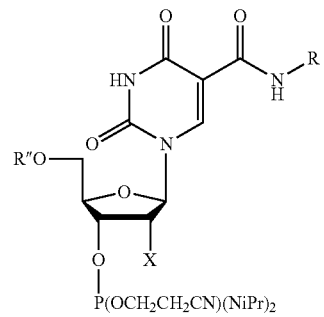

wherein

R" is selected from the group consisting of H, DMT and triphosphate (—P(O)(OH)—O—P(O)(OH)—O—P(O)(OH)$_2$)or a salt thereof;

X is selected from the group consisting of —H, —OH, —OMe, —O-allyl, —F, —OEt, —OPr, —OCH$_2$CH$_2$OCH$_3$ and -azido;

R is selected from the group consisting of —(CH$_2$)$_n$—$^{X1}$;

R$^{X1}$ is selected from the group consisting of:

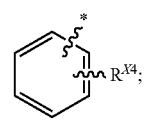

R$^{X4}$ is; and n=0–10.

3. A 5'-triphosphate of a C-5 modified aminocarbonylpyrimidine having the following structure:

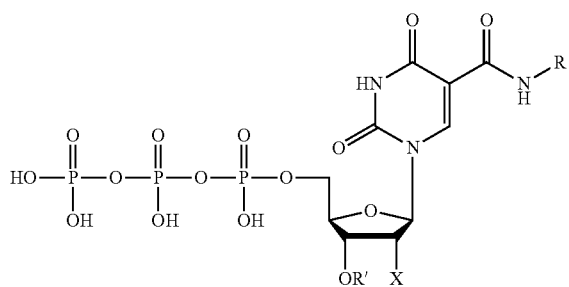

wherein

R' is selected from the group consisting of —H, —Ac, —Bz, —CH$_2$CH$_2$OCH$_3$, —C(O)CH$_2$OCH$_3$ and —SiMe$_2$tBu;

X is selected from the group consisting of —H, —OH, —OMe, —O-allyl, —F, —OEt, —OPr, —OCH$_2$CH$_2$OCH$_3$ and -azido;

R is selected from the group consisting of —(CH$_2$)$_n$—R$^{X1}$;

R$^{X1}$ is selected from the group consisting of:

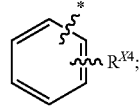

R$^{X4}$ is; and n=0–10.

* * * * *

UNITED STATES PATENT AND TRADEMARK OFFICE
CERTIFICATE OF CORRECTION

PATENT NO. : 9,163,056 B2  
APPLICATION NO. : 14/069798  
DATED : October 20, 2015  
INVENTOR(S) : John Rohloff et al.

Page 1 of 1

It is certified that error appears in the above-identified patent and that said Letters Patent is hereby corrected as shown below:

IN THE CLAIMS

Column 34, line 34 -- "$R^{X4}$ is" should read "$R^{X4}$ is -F"

Column 34, line 66 -- "$R^{X4}$ is" should read "$R^{X4}$ is -F"

Column 36, line 16 -- "$R^{X4}$ is" should read "$R^{X4}$ is -F"

Signed and Sealed this  
Twenty-ninth Day of March, 2016

Michelle K. Lee  
*Director of the United States Patent and Trademark Office*